(12) United States Patent
Choi et al.

(10) Patent No.: US 11,693,019 B2
(45) Date of Patent: Jul. 4, 2023

(54) AUTOMATED LIQUID-PHASE IMMUNOASSAY APPARATUS

(71) Applicant: BODITECH MED INC., Chuncheon-si (KR)

(72) Inventors: Eui Yul Choi, Chuncheon-si (KR); Hoo Don Joo, Chuncheon-si (KR); Hyung Hoon Kim, Chuncheon-si (KR); Chuhyun Cho, Chuncheon-si (KR); Uk Bin Im, Chuncheon-si (KR); Young Jin Oh, Chuncheon-si (KR); Youn Tae Im, Chuncheon-si (KR); Ji Woon Jung, Chuncheon-si (KR)

(73) Assignee: BODITECH MED INC., Chuncheon-si (KR)

( * ) Notice: Subject to any disclaimer, the term of this patent is extended or adjusted under 35 U.S.C. 154(b) by 97 days.

(21) Appl. No.: 17/239,416

(22) Filed: Apr. 23, 2021

(65) Prior Publication Data

US 2021/0239722 A1    Aug. 5, 2021

Related U.S. Application Data

(63) Continuation of application No. 16/098,663, filed as application No. PCT/KR2018/001364 on Feb. 1, 2018, now Pat. No. 11,035,869.

(30) Foreign Application Priority Data

Feb. 2, 2017    (KR) .................. 10-2017-0014829

(51) Int. Cl.
*G01N 35/00*    (2006.01)
*B01L 3/00*    (2006.01)
(Continued)

(52) U.S. Cl.
CPC .... *G01N 35/0098* (2013.01); *B01L 3/502715* (2013.01); *G01N 21/6428* (2013.01);
(Continued)

(58) Field of Classification Search
CPC .......... G01N 35/0098; G01N 21/6428; G01N 21/76; G01N 33/54326; G01N 35/04;
(Continued)

(56) References Cited

U.S. PATENT DOCUMENTS 6,207,463 B1    3/2001    Tuunanen
2001/0007770 A1    7/2001    Tajima
(Continued)

FOREIGN PATENT DOCUMENTS

JP    H06242119 A    9/1994
JP    H08122336 A    5/1996
(Continued)

*Primary Examiner* — Samuel P Siefke
*Assistant Examiner* — Henry H Nguyen
(74) *Attorney, Agent, or Firm* — Rabin & Berdo, P.C.

(57) ABSTRACT

Disclosed is an automated liquid-phase immunoassay apparatus used with a cuvette having a plurality of chambers containing a reagent necessary for detection of an analyte in a biological specimen. The apparatus includes a movable cuvette module equipped with the cuvette, an optical reading module for optical assaying of a material resulting from a reaction between the specimen and the reagent, and a dispenser module which is positioned on the cuvette module and which dispenses the specimen and the reagent to the plurality of chambers of the cuvette and washes the specimen and the reagent therefrom.

6 Claims, 15 Drawing Sheets

(51) Int. Cl.
  *G01N 33/543* (2006.01)
  *G01N 35/04* (2006.01)
  *G01N 35/10* (2006.01)
  *G01N 21/64* (2006.01)
  *G01N 21/76* (2006.01)

(52) U.S. Cl.
  CPC ....... *G01N 21/76* (2013.01); *G01N 33/54326* (2013.01); *G01N 35/04* (2013.01); *G01N 35/10* (2013.01); *B01L 2300/0654* (2013.01); *B01L 2300/0663* (2013.01); *G01N 2035/00574* (2013.01); *G01N 2035/0401* (2013.01)

(58) Field of Classification Search
  CPC ......... G01N 35/10; G01N 2035/00574; G01N 2035/0401; G01N 21/645; G01N 33/536; G01N 2035/0484; G01N 2035/103; G01N 35/02; G01N 33/53; B01L 3/502715; B01L 2300/0654; B01L 2300/0663
  See application file for complete search history.

(56) References Cited

U.S. PATENT DOCUMENTS

| | | |
|---|---|---|
| 2006/0281094 A1 | 12/2006 | Squirrell et al. |
| 2007/0172390 A1 | 7/2007 | Ootani et al. |
| 2008/0240994 A1* | 10/2008 | Shohmi ................ G01N 35/10 422/400 |
| 2011/0124029 A1 | 5/2011 | Remes et al. |
| 2012/0122231 A1 | 5/2012 | Tajima |
| 2014/0170735 A1 | 6/2014 | Holmes |
| 2014/0320862 A1 | 10/2014 | Kim et al. |

FOREIGN PATENT DOCUMENTS

| | | | |
|---|---|---|---|
| JP | 2007192766 A | 8/2007 | |
| JP | 2008014638 A | 1/2008 | |
| KR | 100148239 B1 | 8/1998 | |
| KR | 101149357 B1 | 5/2012 | |
| KR | 1020150056479 A | 5/2015 | |
| KR | 1020160134542 A | 11/2016 | |
| WO | 90/01168 A2 | 2/1990 | |
| WO | WO-2011074456 A1 * | 6/2011 | ............ B01L 3/0275 |

* cited by examiner

AUTOMATED LIQUID-PHASE IMMUNOASSAY APPARATUS

CROSS-REFERENCE TO THE RELATED APPLICATIONS

This is a continuation of U.S. application Ser. No. 16/098,663 filed on Nov. 2, 2018, which is, in turn, a national stage of PCT application number PCT/KR2018/001364, filed on Feb. 1, 2018. Furthermore, this application claims the foreign priority benefit of Korean application number 10-2017-0014829, filed on Feb. 2, 2017. The disclosures of these prior applications are incorporated herein by reference.

TECHNICAL FIELD

The present application relates to an assay system or apparatus for detecting a specific component contained in a biological specimen using an ELISA (enzyme-linked immunosorbent assay) liquid-phase immunoassay.

BACKGROUND ART

As medical and biotechnological fields and various related technologies have been developed, inspections for detecting various molecular indicators such as blood corpuscles, genes, proteins, antigens, and pathogens, in a predetermined biological specimen such as urine and blood have been widely practiced. The inspection process is generally performed by sampling a specimen, reacting the sampled specimen with a predetermined reagent suitable for a target indicator, and assaying and observing the change that occurs. This allows qualitative and/or quantitative assays of the various molecular indicators contained in the specimen, and information on the diagnosis, progress states, or prognosis of diseases may be obtained based on such assays.

One of the technologies widely used in such an inspection process is an immunoreaction technology called EIA (enzyme immunoassay) based on specific bonding between antigens/antibodies. Examples thereof include a color-change measurement method (chromogenic or colorimetric) for measuring a chromogenic reaction using absorbance, a chemiluminescent method, and a method using fluorescence, depending on the type of substrates used for the detection of the analyte. Other examples thereof include a sandwich-type immunoreaction or a competitive-type immunoreaction, which is also called an enzyme-linked immunosorbent assay method, depending on the method of assay.

In the assays, it is preferable to remove non-specific reactants for detection with high sensitivity and high specificity regardless of the method that is used. That is, in order to accurately detect the material resulting from the reaction after the reaction between the reagent and the specimen in the inspection process, it is necessary to purify or separate the material resulting from the reaction. However, in many cases, the detection of reaction results requires the use of a membrane such as nitrocellulose or the use of a two-dimensional flat plate. However, the use of such membranes or plates not only limits the reaction area, but also makes it difficult to remove non-specific reactants.

The most effective way to remove the non-specific reactants is a physical washing or purification method. Therefore, it is necessary to develop an apparatus/system that is capable of accurately and quickly performing a plurality of inspections for a reaction between a predetermined amount of a specimen and a reagent, the physical purification of the material resulting from the reaction, and detection and reading/assay thereof using one integrated system.

DISCLOSURE

Technical Problem

The present application provides an apparatus or a system that is optimized for integrated performance of a reaction between a specimen and a reagent, purification/separation of the material resulting from the reaction, and detection/reading/assay of the material resulting from the reaction using a liquid-phase-based enzyme-linked immunoassay method with respect to a plurality of specimens.

Technical Solution

Provided is an automated liquid-phase immunoassay apparatus used with a cuvette having a plurality of chambers (or wells) containing a reagent necessary for detection of an analyte in a biological specimen. The automated liquid-phase immunoassay apparatus includes:

a movable cuvette module equipped with the cuvette, an optical reading module for optical assaying of a material resulting from a reaction between the specimen and the reagent, and a dispenser module positioned over the cuvette module for dispensing the specimen and the reagent to the plurality of chambers of the cuvette and washing the specimen and the reagent therefrom.

The cuvette module includes:

a holder being displaceable and having an equipment channel for receiving the cuvette, a remover module located over the holder for removing a dispensing tip connected to the dispenser module, and a standard block fixed to the holder to thus move integrally with the holder, the standard block having an optical hole formed therethrough in upward and downward directions, a predetermined optical means being embedded in the hole, and the holder having one or more inspection holes through which at least a portion of the equipment channel is open in a downward direction so that the cuvette received in the equipment channel is exposed to the optical reading module.

The dispenser module includes:

a driving unit, a dispenser unit connected to one side of the driving unit and movable in a horizontal direction between the one side and another side of the driving unit, and a pump unit fixed to the another side of the driving unit, the dispenser unit including a magnetic beam and an arm unit, upper and lower locations of the magnetic beam being fixed, the arm unit includes an up-and-down moving body, a sampling arm detachably fitted with the predetermined dispensing tip at a bottom end thereof, a punching arm for opening a sealing film of the cuvette by punching, and a straw arm having upper and lower hollows formed in upward and downward directions therein and being detachably fitted with a cup-shaped washing tip including a non-magnetic material at a bottom end thereof, the sampling arm, the punching arm, and the straw arm are connected to the up-and-down moving body to thus be integrally displaced upwards and downwards together with the up-and-down moving body, the magnetic beam being introduced into the upper and lower hollows in the straw arm and relatively displaceable in upward and downward directions with respect to the straw arm, the sampling arm being connected to the pump unit to thus dispense the specimen and the reagent to the chambers of the cuvette, and the optical assaying by the optical reading module includes detection of a fluorescent signal, a visible color, or a chemiluminescent signal.

In particular, the holder is moved in forward and backward directions, the standard block is fixed to a rear end of the holder to thus be integrally displaced together with the holder, and the optical reading module is positioned on a path of front-and-rear-direction movement of the holder.

In particular, the holder further includes a heat plate for maintaining the temperature of the cuvette equipped therein at a lower part of the holder. The heat plate keeps the temperature of the reaction performed in the cuvette constant at the desired temperature so that the reaction takes place efficiently.

In particular, the optical reading module may or may not include a light source, and may be located below the holder, thus scanning or capturing signals of the standard block through the optical hole and also signals of the material resulting from the reaction in the cuvette through the inspection holes. The signals of the standard block may be used to accurately detect the analyte by correcting deviations between the apparatuses.

In an embodiment, the optical reading module includes a light source capable of sufficiently exciting a fluorescent material of the material resulting from the reaction for measurement of the fluorescent signal, the predetermined optical means included in the standard block is a fluorescent standard material, and a standard signal sensed in the standard block and the signal sensed in the material resulting from the reaction may be fluorescent signals. In this case, the optical assaying includes comparing the standard signal sensed in the standard block and the fluorescent signal detected in the material resulting from the reaction so as to correct deviation in a detected signal between a plurality of apparatuses.

In another embodiment, the optical reading module includes a light source capable of emitting an absorption wavelength region band suitable for absorbance measurement of the visible color, the predetermined optical means included in the standard block is a standard material for the absorbance measurement, and a standard signal sensed in the standard block and a signal sensed in the material resulting from the reaction may be a color signal of a visible-ray region. In this case, the optical assaying includes comparing the standard signal sensed in the standard block and the signal detected in the material resulting from the reaction so as to correct deviation in a detected signal between a plurality of apparatuses.

In yet another embodiment, the optical module does not include a light source, the signal sensed in the material resulting from the reaction may be a chemiluminescent signal, and the standard block is not used. That is, the optical assaying by the optical reading module includes the detection of the chemiluminescent signal of the material resulting from the reaction. In this case, the optical reading module does not include a light source, and the standard block is not used in the optical assaying by the optical reading module. In this respect, another aspect of the present application provides an apparatus in which a holder is not provided with a standard block.

In particular, the remover module includes a remover plate which has a plurality of holes formed therethrough upwards and downwards and which is displaceable in leftward and rightward directions or in a lateral direction, and the sampling arm, the punching arm, and the straw arm are located so as to pass through the plurality of holes from a top to a bottom of the remover plate.

In particular, one to six equipment channels, and particularly three equipment channels, are included in the holder, and three different types of inspections on three different types of specimens or the same specimen are possible.

In particular, when a plurality of cuvettes is used, a set of a dispensing tip and a washing tip may be used without having to replace the tip for each cuvette during an intermediate step of the reaction. To this end, the cuvette includes a dispensing-tip-fitting hole and a washing-tip-fitting hole.

In particular, the cuvette sequentially includes fitting holes, in which the dispensing tip and the washing tip are seated, and chambers. With respect to the chambers, the cuvette sequentially includes a specimen-filling chamber which is filled with a target specimen to be inspected, a buffer-solution-and-dilution chamber which is filled with a reagent necessary for inspecting the specimen and in which the specimen is diluted, a reaction chamber in which a reaction between the specimen and the reagent occurs, a washing chamber which is filled with a washing solution and in which washing is performed, and a detection chamber for reading the material resulting from the reaction, that is, for scanning the fluorescent signal of the material resulting from the reaction. Optionally, for convenience of the user, the specimen-filling chamber may be located in front of the dispensing-tip-fitting hole and the washing-tip-fitting hole. In this case, convenience is increased when the cuvette is filled with the target biological specimen to be inspected after the cuvette is conveyed into the apparatus according to the present application.

The punching arm, the sampling arm, and the straw arm of the arm unit included in the dispenser module of the apparatus according to the present application may be connected to the up-and-down moving body so as to be integrally displaced in upward and downward directions together with the up-and-down moving body. The cuvettes having the chambers provided in either of the above-described two arrangements may be contained therein.

Another aspect of the present application provides an apparatus that is capable of detecting chemiluminescent signals and does not include a standard block, unlike the apparatus described above.

In this respect, the apparatus according to the present application may or may not include the standard block.

The above-described apparatus is an automated liquid-phase immunoassay apparatus which is used with a cuvette having a plurality of chambers containing a reagent necessary for detection of an analyte in a biological specimen and which is capable of detecting a chemiluminescent signal. The automated liquid-phase immunoassay apparatus includes:

a movable cuvette module equipped with the cuvette, an optical reading module for optical assaying of a material resulting from a reaction between the specimen and the reagent, and a dispenser module positioned over the cuvette module for dispensing the specimen and the reagent to the plurality of chambers of the cuvette and washing the specimen and the reagent therefrom.

The cuvette module includes:

a holder, being displaceable and having an equipment channel for receiving the cuvette, and a remover module located over the holder for removing a dispensing tip connected to the dispenser module, and the holder has one or more inspection holes through which at least a portion of the equipment channel is open in a downward direction so that the cuvette received in the equipment channel is exposed to the optical reading module.

The dispenser module includes:

a driving unit, a dispenser unit connected to one side of the driving unit and movable in a horizontal direction between the one side and another side of the driving unit, and a pump unit fixed to the another side of the driving unit, the dispenser unit including a magnetic beam and an arm unit, upper and lower locations of the magnetic beam being fixed, the arm unit including an up-and-down moving body, a sampling arm detachably fitted with the predetermined dispensing tip at a bottom end thereof, a punching arm for opening a sealing film of the cuvette by punching, and a straw arm having upper and lower hollows formed in upward and downward directions therein and being detachably fitted with a cup-shaped washing tip including a non-magnetic material at a bottom end thereof, the sampling arm, the punching arm, and the straw arm being connected to the up-and-down moving body to thus be integrally displaced upwards and downwards together with the up-and-down moving body, the magnetic beam being introduced into the upper and lower hollows in the straw arm and relatively displaceable in upward and downward directions with respect to the straw arm, the sampling arm being connected to the pump unit to thus dispense the specimen and the reagent to the chambers of the cuvette, the optical reading module does not include a light source, and the optical assaying by the optical reading module includes detecting the chemiluminescent signal of the material resulting from the reaction.

In particular, the holder may be moved in forward and backward directions, and the optical reading module may be positioned on a path of front-and-rear-direction movement of the holder.

In particular, the optical reading module may be located below the holder, thus optically assaying the material resulting from the reaction in the cuvette through the inspection holes.

In particular, the holder may further include a heat plate for maintaining the temperature of the cuvette equipped therein at a lower part of the holder.

In particular, the apparatus includes a remover plate which has a plurality of holes formed therethrough upwards and downwards and which is displaceable leftwards and rightwards. The sampling arm, the punching arm, and the straw arm are located so as to pass through the plurality of holes from a top to a bottom of the remover plate.

In particular, one to six, and particularly three, equipment channels for receiving the cuvette of the holder may be included.

In particular, the cuvette may sequentially include a dispensing-tip-fitting hole and a washing-tip-fitting hole in which the dispensing tip and the washing tip are seated, a specimen-filling chamber, a buffer-solution-and-dilution chamber, a reaction chamber, a washing chamber for washing, and a detection chamber for detecting the fluorescent signal of the material resulting from the reaction.

In particular, the cuvette sequentially includes a specimen-filling chamber, a dispensing-tip-fitting hole and a washing-tip-fitting hole in which the dispensing tip and the washing tip are seated, a buffer-solution-and-dilution chamber, a reaction chamber, a washing chamber for washing, and a detection chamber for detecting the fluorescent signal of the material resulting from the reaction.

Another aspect of the present application is directed to a method of assaying a particular analyte included in a biological specimen using the apparatus described in the present application, and may include steps according to the operating method described in the specification of the present application.

Advantageous Effects

In the automated liquid-phase fluorescence immunoassay apparatus according to the present invention, dispensing and reaction between a specimen and a reagent, and separation (purification) of the material resulting from the reaction by a washing module using magnetic beads are integrally performed, and it is possible to detect/read the materials resulting from the reaction with higher sensitivity and higher specificity using a liquid-phase specimen optical system than when using conventional methods.

In particular, according to the present invention, the inspections for the detection and reading/assay of the material resulting from the reaction after the distribution of the specimen and the reaction between the reagent and the specimen are performed accurately and quickly using a single integrated system. Accordingly, it is possible to reduce an inspection time, improve the accuracy and reproducibility of the inspection, and reduce the steps included in the entire inspection and the input costs.

Further, the automated liquid-phase immunoassay apparatus according to the present application has a holder having a plurality of equipment channels, so that a plurality of cuvettes is bonded to one holder and multiple diagnoses and assays are simultaneously performed in one system. Therefore, it is possible to quickly perform various inspections and diagnoses/assays for the purpose of accurate diagnosis at the site for inspection and treatment, thereby saving time, costs, and manpower.

The housing included in the automated liquid-phase immunoassay apparatus according to the present application is capable of blocking the inflow of foreign materials to thus perform more accurate specimen inspection. In addition, since, together with a driving unit that provides the up-and-down and left-and-right moving force, an optical reader is provided on the path of the left-and-right movement of the cuvette, it is possible to perform specimen inspection with a quick and simple operation.

Further, the pump unit included in the automated liquid-phase immunoassay apparatus according to the present application is capable of accurately adjusting the amount of the specimen, the reagent, or the material resulting from the reaction upon suction or discharge thereof using a dispensing tip.

Further, the pulley-belt-type front-and-rear driving part included in the automated liquid-phase immunoassay apparatus according to the present application is capable of preventing the occurrence of vibrations and the inflow of foreign materials caused by friction generated when moving leftwards and rightwards, unlike a gear type, thereby enabling more accurate inspection.

Further, the arm unit provided in the automated liquid-phase fluorescence immunoassay apparatus according to the present application includes an integrated module that is integrally provided with a punching arm, a sampling arm, and a straw arm, which enables the control of locations in upward and downward directions using one driving motor upon dispensing of a pump (pump dispenser), driving of a puncher, and separation of a washing-and-dispensing tip and a washing tip. Therefore, it is possible to reduce the size and manufacturing costs, unlike the case where each module is constituted by a respective driving motor.

In addition, in the apparatus according to the present application, when a plurality of cuvettes is used, a set of a dispensing tip and a washing tip is capable of being used without having to replace the tip for each cuvette during an intermediate step of the reaction. It is possible to easily remove the tip using a remover module.

Further, since the apparatus according to the present application includes a standard block, it is possible to reduce deviation in signal values between the apparatuses.

BEST MODE

Figure 1:
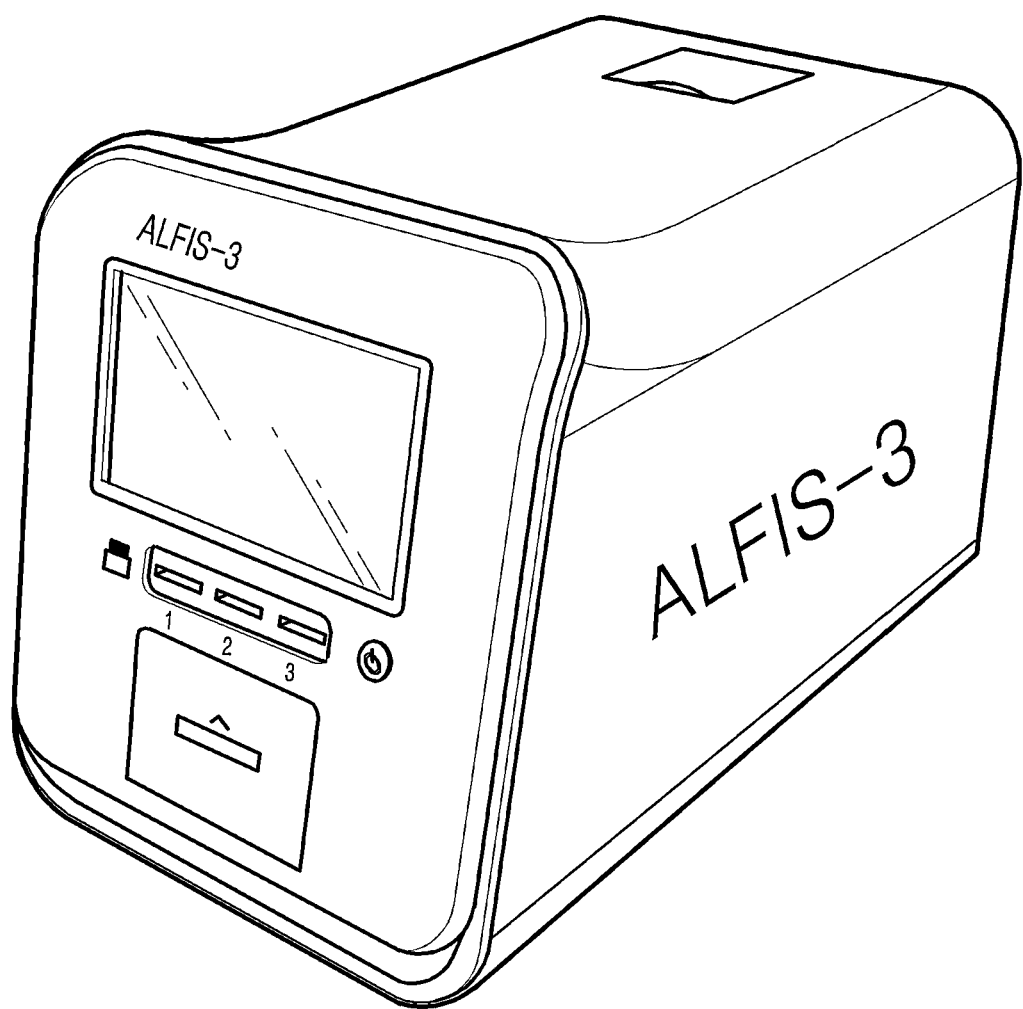
FIG. 1 is a photograph showing the appearance of an apparatus actually manufactured according to an embodiment of the present application.

Hereinafter, preferred embodiments according to the present invention will be described with reference to the accompanying drawings. The present embodiments are illustrative and not intended to limit the invention in any way.

The terms "below", "rear surface", "on", and "upper part", which are spatially relative terms, may be used to easily designate a correlation between one member or constituents and other elements or constituents, as shown in the drawings. Spatially relative terms should be understood to include, in addition to the directions shown in the drawings, terms that include different directions of the element during use or operation thereof. For example, when reversing a member shown in the drawings, a member described as being "below" or "beneath" another member may be placed "on" the another member. Therefore, the exemplifying term "below" may include both downward and upward directions. The members may be oriented in different directions, so that spatially relative terms may be interpreted according to orientation. For example, "leftward and rightward directions" may be interpreted as "upward and downward directions" without being limited thereto.

In the present specification, spatially relative terms indicate the orientation when looking at the front surface of the apparatus according to the present application.

In the present specification, the angles and directions mentioned in the description of the structure of the present invention are based on those shown in the drawings. In the description of the structure constituting the present invention in the specification, when reference points and locational relationships with respect to angles are not explicitly stated, reference is to be made to the relevant drawings.

Hereinafter, the terms used in the present specification and the principle of the chemical reaction used together with the present apparatus will be first described.

In the present specification, the term "detection" means quantitative or qualitative analysis of a material resulting from the reaction between a reagent and a specimen, or an analyte contained in a purified material after the material resulting from the reaction is purified in order to determine the presence or absence or the amount of the analyte included in the specimen, as will be described later. The detection results are read in the automated liquid-phase immunoassay apparatus 1 according to the present invention.

In the present specification, the term "inspection" is used as a term including all of detection, assaying, and reading.

The term "specimen" as used in the present specification refers to a composition that is expected to include an analyte, and the specimen that may be used in the present invention is a liquid phase or fluidic material similar to a liquid. In an embodiment according to the present invention, the specimen is a biological specimen, and may be a living-body-derived body composition such as whole blood, blood plasma, serum, urine, saliva, human excreta, and cell extracts.

The term "analyte" used in the present specification is a target compound to be assayed in the specimen, and is also referred to as a target or an indicator, and includes, but is not limited to, a protein component such as an antigen or a nucleic acid material such as a gene.

In the present specification, the term "reagent" refers to a material to be mixed with the specimen for quantitative or qualitative assay of the analyte contained in the specimen. The type of reagent depends on the specific type of analyte. Examples thereof may include a reaction buffer solution or a buffer, a dilution buffer, a detection buffer, a washing buffer, or predetermined antibodies, enzymes, or substrates that react with various materials, e.g., an antigen, in the specimen, but are not limited thereto.

FIG. 1 shows the appearance of an apparatus 1 manufactured in an embodiment according to the present application.

Figure 2:
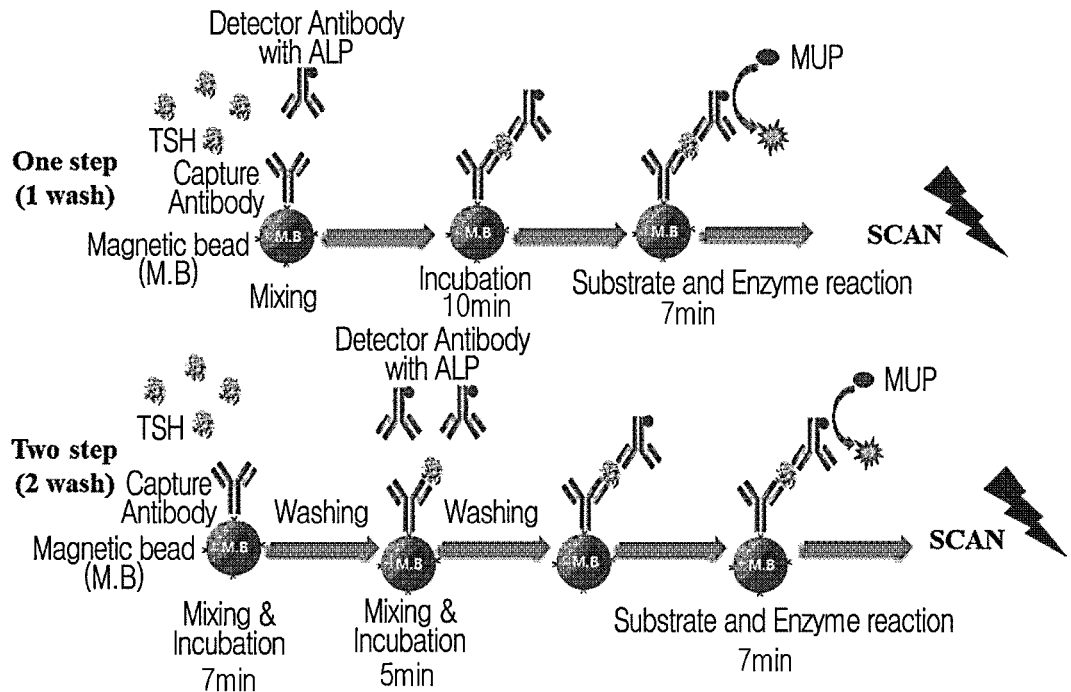
FIG. 2 is a mimetic diagram showing a process of sandwich immunoreaction using magnetic beads used in the apparatus according to the embodiment of the present application.
Figure 3:
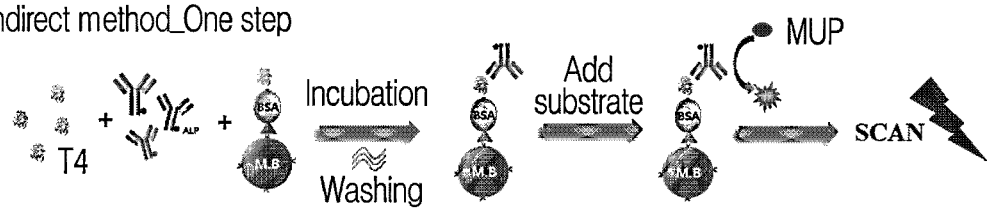
FIG. 3 is a mimetic diagram showing a process of competitive immunoreaction using magnetic beads used in the apparatus according to the embodiment of the present application.
Figure 3:
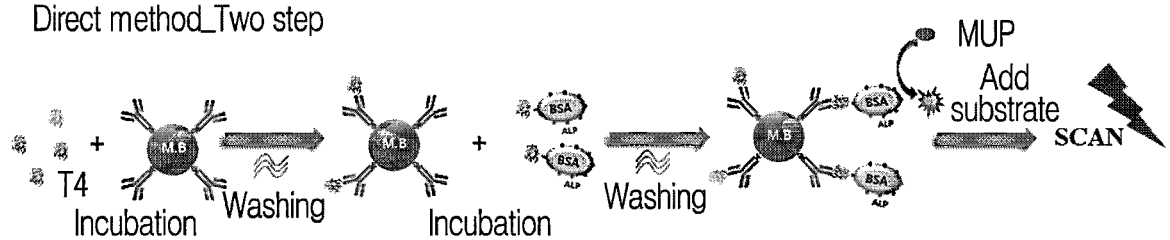

The automated liquid-phase immunoassay apparatus 1 according to the present invention is an apparatus that is optimized for the detection of a special component or an analyte contained in a biological specimen, and is also optimized for physical washing using magnetic beads for the purpose of separation of unreacted materials from the material resulting from the reaction prior to detection of the analyte using an immunoassay (ELISA)-based reaction on the basis of specific bonding between antigens/antibodies, for example, the reactions shown in FIGS. 2 and 3.

FIGS. 2 and 3 show various ELISA assay processes for assaying the analytes. A sandwich immunoreaction (sandwich immunoassay) refers to an immunoreaction in the form of sandwich bonding of a capture antibody and a detector antibody, and an enzyme is chemically bonded to the detector antibody to thus induce a quantitative reaction with the substrate. The capture antibody is chemically or physically bonded to the magnetic beads, and the detector antibody adopts a conjugate bonded to the enzyme. The sandwich reaction using the magnetic beads may be broadly divided into two types, and is divided into a one-step reaction (one-step assay) or a two-step reaction (two-step assay) depending on the number of washing steps. The two-step reaction is a method in which the specimen and the capture antibody are first reacted, washing is performed, and the detector antibody is then reacted therewith. The one-step reaction is a method in which the capture antibody and the detector antibody are simultaneously reacted without separation thereof (FIG. 2).

The competition reaction (competition assay), which is frequently used to detect a small amount of protein molecules together with the sandwich immunoreaction, is also divided into two methods. The competition reaction is divided into an indirect competition reaction or a direct competition reaction depending on whether competitive proteins or antibodies are conjugated to magnetic beads, and is divided into a one-step reaction and a two-step reaction depending on the number of steps of the immunoreaction. For example, FIG. 3 shows the form of the indirect competition reaction and the form of the direct competition reaction among the competition reactions.

In the embodiment according to the present application, a fluorescent signal is used to detect the material resulting from the reaction. In this case, for example, an enzyme-substrate reaction including ALP (alkaline phosphatase) and MUP (4-methylumbelliferyl phosphate) is used. ALP, which is a kind of enzyme, is a representative enzyme that causes a dephosphorylation reaction. 4-MUP is reacted with ALP to thus perform irreversible dephosphorylation due to enzymatic hydrolysis, which generates 4-MU (4-methylumbelliferone). 4-MU (4-methylumbelliferone) is excited at a wavelength of 360 nm to thus have characteristic fluorescence whereby a wavelength of 450 nm is emitted. The intensity of this fluorescent signal is detected and then used to determine the concentration of the analyte in the specimen.

In another embodiment according to the present application, color changes (colorimetric methods) are used to detect the material resulting from the reaction. The color change assay serves to detect a change in the visible color with respect to absorption of light by the material resulting from the reaction at a specific visible-ray wavelength, the absorbance is detected using the signal of the material resulting from the reaction, and the detected value is used to determine the concentration of the analyte in the specimen. For example, representative examples of enzymes and substrates may include peroxidases and substrates thereof, that is, TMB (3,3',5,5' tetramethylbenzidine), DAB (3,3',4,4' diaminobenzidine), 4CN (4-chloro-1-naphthol), ABTS (2,2'-azino-di[3-ethyl-benzthiazoline]sulfonate), and OPD (o-phenylenediamine), but are not limited thereto. For example, when TMB is used as a substrate, a blue color is generated, which may be detected using light having a wavelength of 650 nm. ABTS generates a blue-green color, which may be detected using light of 405 to 410 nm. Other examples of the enzymes and the substrates may include ALP and substrates thereof, that is, BCIP/NBT (5-bromo-4-chloro-3-indolyl-phosphate/nitroblue tetrazolium) and p-NPP (p-nitro-phenylphosphate), but are not limited thereto. These examples generate a deep yellow color, which may be detected using light having a wavelength of 405 to 410 nm.

In yet another embodiment of the present application, chemiluminescence is used to detect the material resulting from the reaction. The chemiluminescence is the light emitted while excited electrons generated by chemical reactions return to a ground state. A light source is not required, and the chemiluminescence is measured in RLUs (relative light units) per time to determine the concentration of the analyte in the specimen. For example, examples of enzymes and substrates may include peroxidases and substrates thereof, such as luminol, polyphenols (including, for example, pyrogallol, purpurogallin, gallic acid, and umbelliferone), and acridine esters or luciferin (also referred to as bioluminescence, if used), but are not limited thereto. Other examples of the enzymes and the substrates may include ALP and AMPPD (3-(2'-spiroadamantyl)-4-methoxy-4-(3"-phosphoryloxy)-phenyl-1,2-dioxetane), but are not limited thereto.

In this assay, particularly, high-sensitivity and high-specificity detection is required, and for this, the removal of non-specific or unreacted materials is required. That is, in the inspection process, the materials resulting from the reaction need to be purified or separated in order to accurately detect the materials resulting from the reaction between the reagent and the specimen, and the apparatus according to the present application is an apparatus optimized for effective removal of such unreacted materials.

Specifically, in the embodiment, the apparatus according to the present application is an apparatus that is optimized for detection of the signal of the material resulting from the reaction obtained by removing the unreacted materials using physical washing with magnetism, separating only the material resulting from the specific reaction using a permanent magnet to thus form magnetic beads so that concentration is performed, selectively bonding a detector, to which an enzyme is attached, to the material resulting from this reaction, and finally reacting the enzyme with the substrate.

The above-described reaction used in the apparatus according to the present application is performed in a liquid state in a cuvette equipped in the apparatus. The apparatus according to the present application is optimized for performing the above-described reaction in the cuvette and for performing the reaction steps optimized in consideration of the characteristics of various parameters of the reaction performed to detect the material resulting from the reaction.

First, a cuvette 10 used in an automated liquid-phase immunoassay apparatus 1 according to the present invention will be described.

Figure 4:
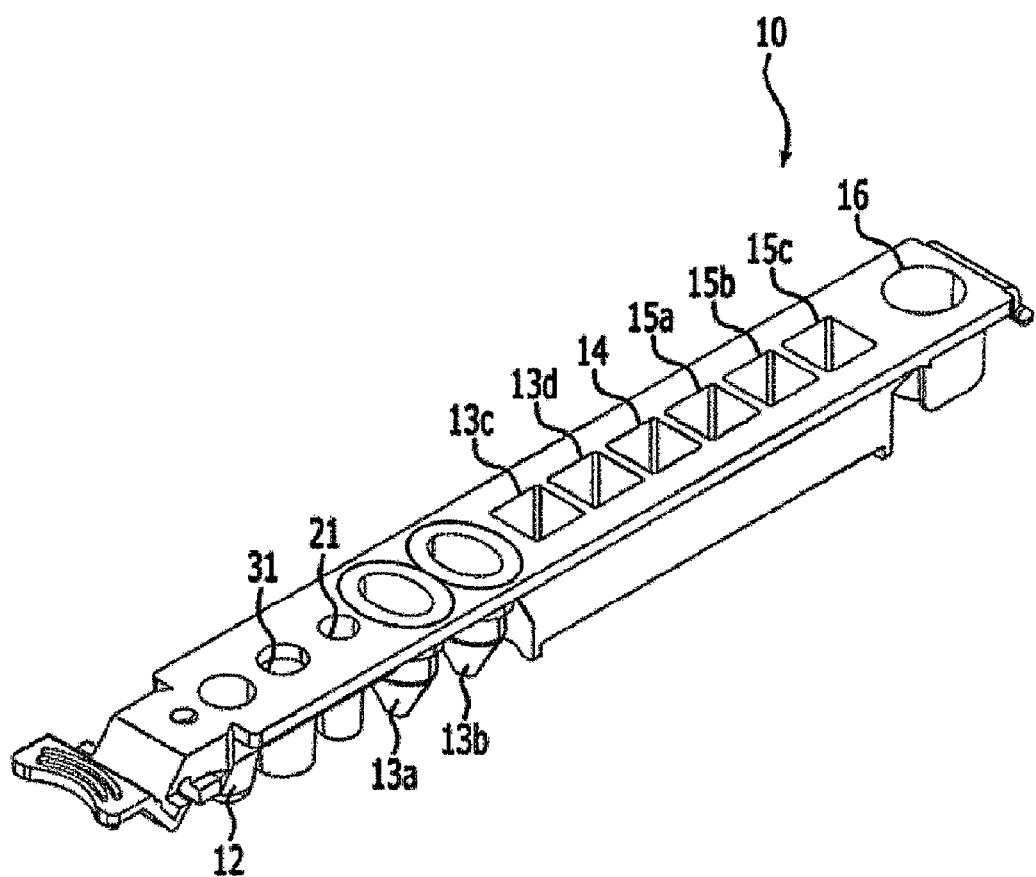
FIG. 4 is a view showing the structure of a cuvette according to the embodiment of the present application used in the apparatus according to the embodiment of the present application.
Figure 5:
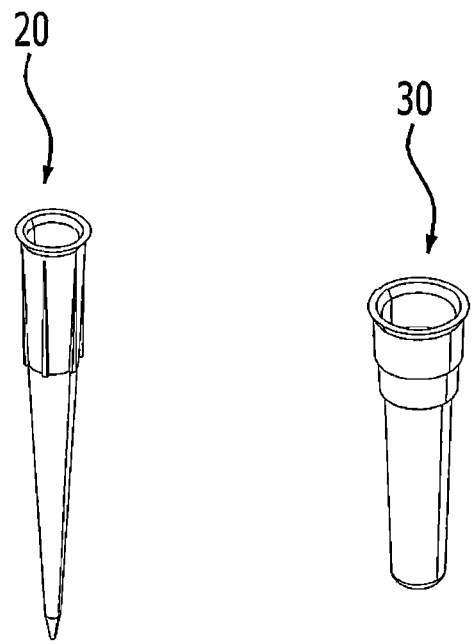
FIG. 5 is a view showing a dispensing tip and a washing tip which are used while being fastened to the cuvette according to the embodiment of the present application used in the apparatus according to the embodiment of the present application.
Figure 6:
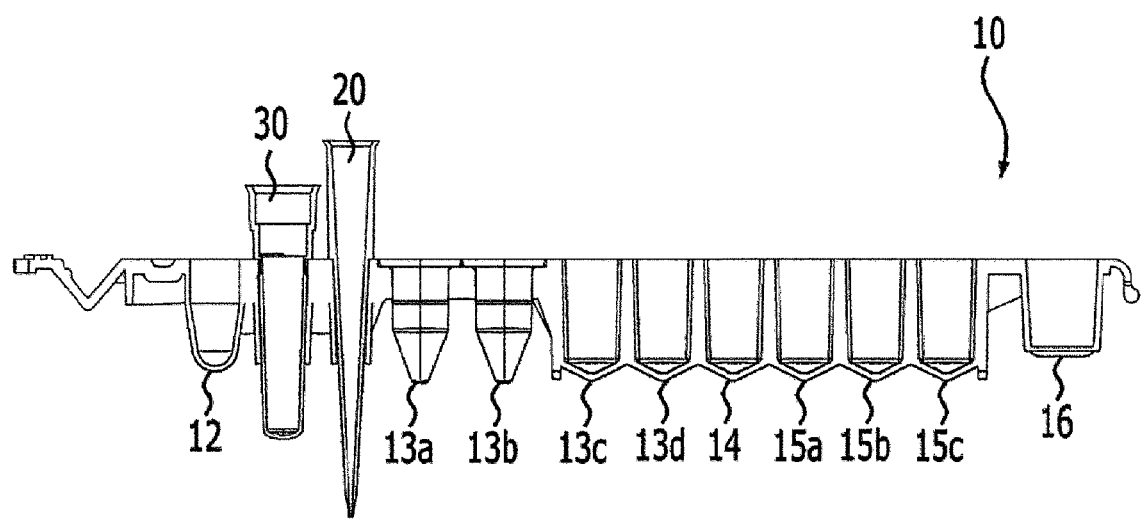
FIG. 6 is a view showing one form of the cuvette equipped with the dispensing tip and the washing tip used in the apparatus according to the embodiment of the present application.

FIG. 4 is a view showing the structure of the cuvette used in the automated liquid-phase immunoassay apparatus according to the present invention, FIG. 5 is a view showing a dispensing tip 20 and a washing tip 30 used in the automated liquid-phase immunoassay apparatus according to the present invention, and FIG. 6 is a view showing the equipment of the dispensing tip 20 and the magnetic or washing tip 30 in the cuvette 10 used in the automated liquid-phase immunoassay apparatus according to the present invention.

The cuvette 10 used in the automated liquid-phase immunoassay apparatus 1 according to the present invention is used for the reaction for the detection of the analyte contained in the specimen. In the cuvette, the reaction between the specimen and the reagent is performed, and the material resulting from the reaction is generated and washed.

The cuvette 10 used in the automated liquid-phase immunoassay apparatus 1 according to the present invention may have an elongated shape extending in forward and backward directions, as shown in FIGS. 4 and 6. Further, the cuvette 10 may include one or more fitting holes and a plurality of chambers. A chamber may also be referred to as a well.

For the fitting hole, the washing tip 30 and the dispensing tip 20 shown in FIG. 5 are fitted into the fitting hole and are then kept therein until the inspection is started or during the inspection process. With respect to this, a washing-tip-fitting hole 21 and a dispensing-tip-fitting hole 31 are provided.

The chambers may sequentially include a specimen-filling chamber 12, chambers 13a, 13b, 13c, and 13d for a buffer solution and dilution, a reaction chamber 14, a washing chamber 15, and a detection chamber 16.

Alternatively, as shown in FIGS. 4 and 6, the washing-tip-fitting hole 21 and the dispensing-tip-fitting hole 31 may be provided in the chamber next to the specimen-filling chamber 12, and, subsequently, the chambers 13a, 13b, 13c, and 13d for the buffer solution and dilution, the reaction chamber 14, the washing chamber 15, and the detection chamber 16 may be sequentially included.

Alternatively, the chambers 13a and 13b, among the chambers for dilution, may include detachable tubes. In this case, the chambers 13a and 13b may be stored separately from the cuvette and then equipped before use. In another case, only the chambers 13a and 13b may be separated. After a specific reagent is added thereto, the chambers 13a and 13b may be equipped in the cuvette, which increases convenience.

Further, the chamber may be sealed using a predetermined sealing film (not shown) in order to prevent denaturation or contamination of the reagent.

The specimen-filling chamber 12 may be provided so as to be filled with various specimens, for example, a target biological specimen to be assayed, and may be formed at the front or rear of the washing-tip-fitting hole 21 and the dispensing-tip-fitting hole 31, as described above.

The buffer solution (also referred to as a buffer) and dilution chambers 13a, 13b, 13c and 13d are filled with a magnetic (magnetic bead, MB) buffer, a detection buffer, and a specimen dilution buffer necessary for the reaction (13a, 13b, and 13c), and are provided at the rear of the specimen-filling chamber 12 or the washing-tip-fitting hole 21 and the dispensing-tip-fitting hole 31 according to the above-described sequence so that the specimen is diluted (13d).

The reaction chamber 14 is provided so as to perform the reaction between the specimen and the reagent, and is formed at the rear of the chambers for the buffer solution and dilution.

The washing chamber 15 may include a plurality of chambers in which the material resulting from the reaction is washed after the reaction in the reaction chamber. In the embodiment, three chambers 15a, 15b, and 15c are included.

In the detection chamber 16, the material resulting from the reaction, which is generated due to the reaction between the specimen and the reagent, is detected. The detection chamber 16 is provided so as to detect the presence of the analyte in the material resulting from the reaction after washing in the washing chamber 15. The detection chamber 16 may be formed at the rear of the washing chamber 15, and may be light-transmissive to enable detection of a fluorescent signal.

In the embodiment, the cuvette 10 may further include a bar code or a QR code (not shown), which is used while being associated with a chip, to be described below, inserted into the automated liquid-phase immunoassay apparatus 1 of the present invention. In the present invention, the bar code includes UPC-A, UPC-E, EAN, Code 3 of 9, Interleaved 2 of 5, Code 128, UCC/EAN-128, Codabar, PostNet, Pharmacode, or PDF-417, but is not limited thereto, or the bar code includes a 1D bar code or a 2D bar code, but is not limited thereto. The bar code or the QR code is obtained by encoding the type of the analyte depending on the type of the specimen.

The dispensing tip 20 and the washing tip 30 are equipped in the cuvette 10 used in the automated liquid-phase immunoassay apparatus 1 according to the present invention.

The dispensing tip 20 may include a disposable micro-tip (for example, a micropipette tip having a volume of 2 to 1000 µl) which is used while being fastened to a sampling arm 556, as will be described later, in order to distribute or dispense the specimen and/or the reagent to the above-described chambers, that is, from one chamber to another chamber. The dispensing tip 20 may have a tubular shape, and the diameter of the dispensing tip 20 may gradually decrease toward a terminal end thereof, so that the terminal end thereof may have a sharp shape.

The dispensing tip 20 described above may be used together with a device that does not have a separate reagent-supplying apparatus and decontamination means, thereby simplifying the operation of the device.

The dispensing tip and the washing tip may be equipped in each of a plurality of cuvettes used in the apparatus according to the present application, and thus the tips may be used separately for different cuvettes, thereby preventing contamination. In the case of a conventional automation device using a syringe needle made of a metal material, it is required to provide an apparatus for performing washing in order to prevent contamination. Accordingly, there are problems in that the volume thereof is increased due to the constitution of separate apparatuses, a separate process for washing the apparatuses is required, and inspection costs are increased.

In particular, the dispensing tip 20 is seated in the dispensing-tip-fitting hole 21 in the cuvette 10 while being fitted thereinto, and is then fastened to the sampling arm 556, as will be described later, when the inspection process is started, thus enabling suction or discharging for distribution or dispensing of the specimen or the reagent to the chambers together with the pump unit 506. Further, in order to perform the reaction in a second or third cuvette when the reaction occurs in a first cuvette during the inspection process, the dispensing tip used in the first cuvette may be temporarily stored in the fitting hole 21. Accordingly, it is possible to use only one tip for one cuvette until the end of the inspection, without replacing the tip at an intermediate stage. Thus, there are merits in that convenience is secured and a reaction time is reduced. This will be described in more detail in the operation process of the apparatus of the present application.

The washing tip 30 has a tubular shape having a predetermined height and width and is a member having a sealed bottom end, and an introduction hole having a predetermined depth and inner diameter is formed in an upper part thereof. The washing tip 30 may include a non-magnetic material so as to transmit magnetism, and may also include a flexible material so as to facilitate fixing to the washing arm and separation from the washing arm. Further, the washing tip 30 is seated in the washing-tip-fitting hole 21 in the cuvette 10 while being fitted thereinto, and is then fastened to a straw arm 554 when the inspection process is started, thus performing washing, as will be described later. Further, in order to perform the reaction in the second or third cuvette when the reaction occurs in the first cuvette during the inspection process, the washing tip used in the first cuvette may be stored in the fitting hole 31. Accordingly, it is possible to use only one tip for one cuvette. Thus, there are merits in that convenience is secured and a reaction time is reduced. This will be described in more detail in the operation process of the apparatus of the present application.

In the embodiment, three cuvettes according to the present application are used and are optimized for performing three types of assays. For example, with respect to the same biological specimen, examples of three different analytes may include FT4 (free thyroxine), TSH (thyroid stimulating hormone), and T3 (triiodothyronine) for diagnosis pertaining to the thyroid gland, and hCG (chorionic gonadotropin), E3 (estriol), and AFP (alpha fetoprotein) for congenital anomaly tests.

Hereinafter, the automated liquid-phase immunoassay apparatus 1 according to the embodiment of the present invention will be described.

Figure 7:
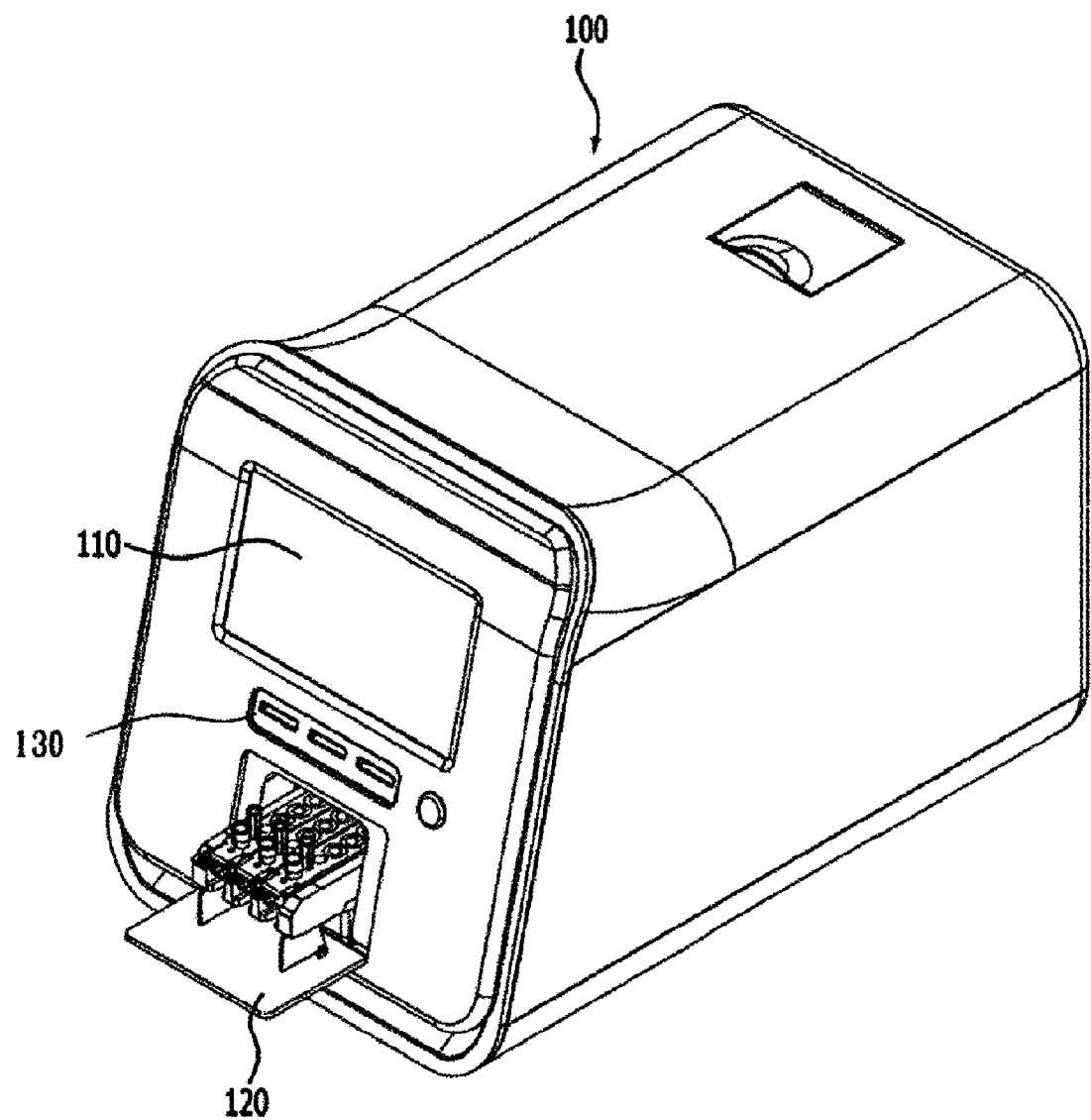
FIG. 7 is a view showing the appearance of the apparatus according to the embodiment of the present application.
Figure 8:
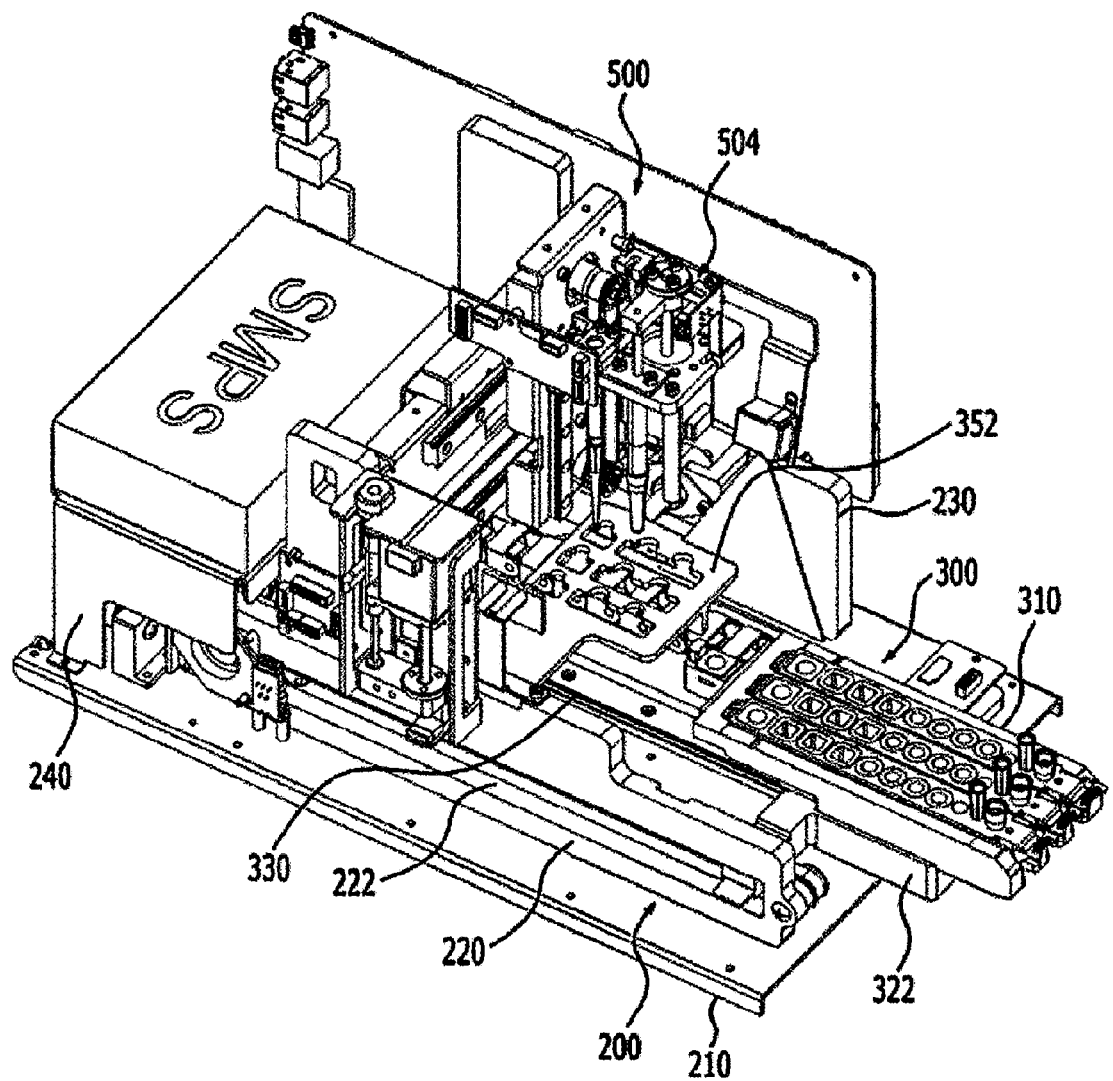
FIGS. 8 and 9 are views showing the apparatus according to the embodiment of the present application, from which a housing is omitted.
Figure 9:
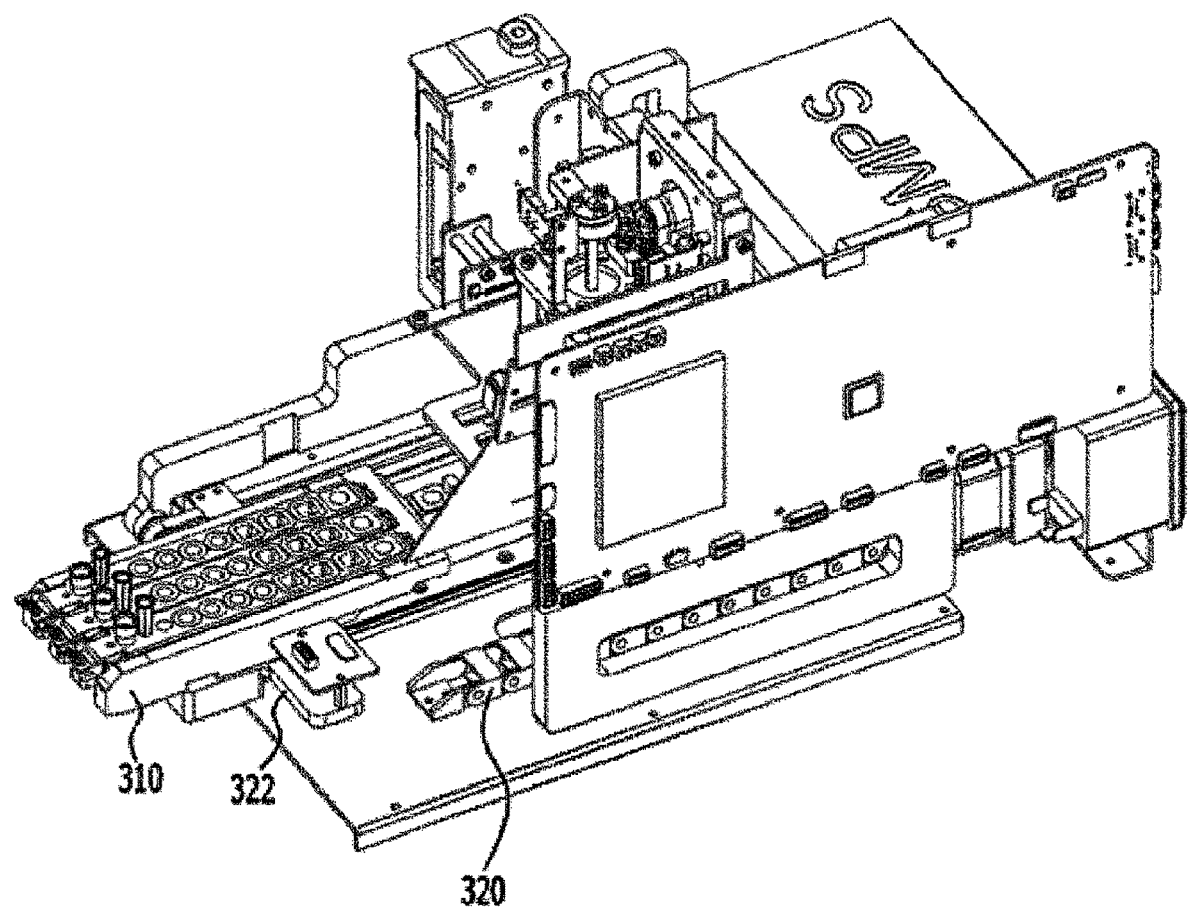

FIG. 7 is a view showing the automated liquid-phase immunoassay apparatus 1 according to the present invention, and FIGS. 8 and 9 are views showing the automated liquid-phase immunoassay apparatus 1 according to the present invention, from which a housing 10 is omitted, in different directions.

The automated liquid-phase immunoassay apparatus 1 according to the embodiment of the present invention is an automated liquid-phase immunoassay apparatus 1 for inspecting a specimen by inserting the cuvette 10, and may include a housing 100, a frame 200, a cuvette module 300, an optical reading module 400, and a dispenser module 500.

The housing 100 constitutes the entire exterior of the automated liquid-phase immunoassay apparatus 1, and functions to block the inflow of foreign materials into the apparatus.

The housing 100 may be provided with various input parts for operation and a display part 110 for output. Further, the housing 100 is provided with an inlet-and-outlet port 120 through which the cuvette 10 is inserted. When the cuvette 10 is inserted into the housing 100 through the inlet-and-outlet port 120, the housing 100 may block the inflow of foreign materials into the chamber included in the cuvette 10, thereby enabling more accurate inspection of specimens.

The frame 200 may be provided in the housing 100 so as to fix the cuvette module 300, the optical reading module 400, and the dispenser module 500. The frame 200 may include a lower frame 210, a first side frame 220, a second side frame 230, and a rear frame 240.

The lower frame 210 is positioned at the lower portion of the automated liquid-phase immunoassay apparatus 1. The lower frame 210 may have a plate-like structure having a predetermined area.

The first side frame 220 and the second side frame 230 may be positioned on the left and right sides of the lower frame 210, respectively, and may be constituted so as to have a predetermined height. In addition, the first side frame 220 and the second side frame 230 may have respective guide spaces 222 and 232 for guiding displacement of the holder 310 in forward and backward directions.

The rear frame 240 may be located at the rear of the apparatus, and may be provided so as to fix a predetermined control apparatus.

Figure 10A:
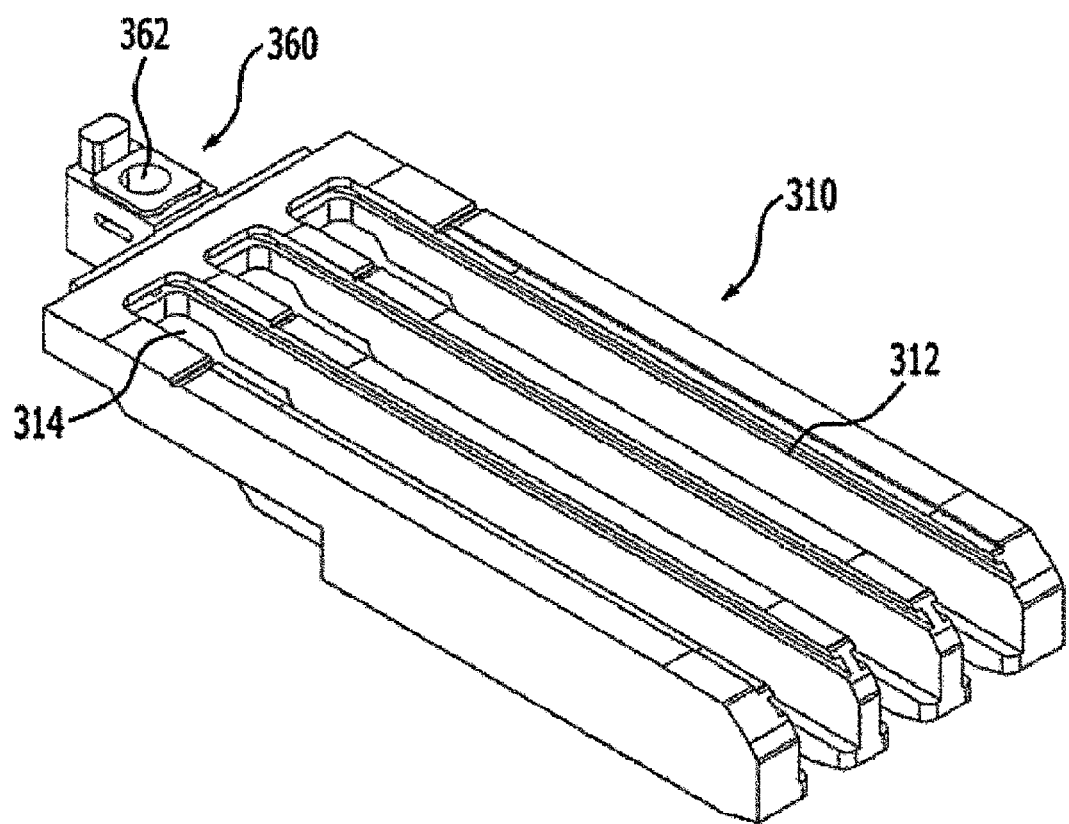
FIGS. 10A, 10B and 11 are views showing a holder and a form in which the cuvette is mounted in the holder in the apparatus according to the embodiment of the present application.
Figure 10B:
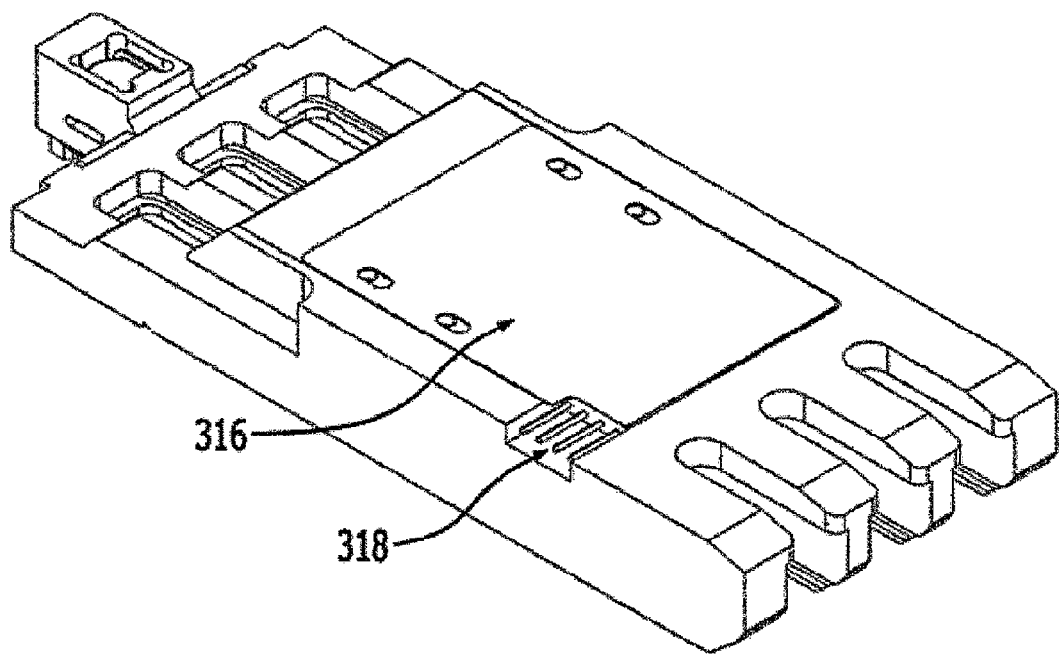
Figure 11:
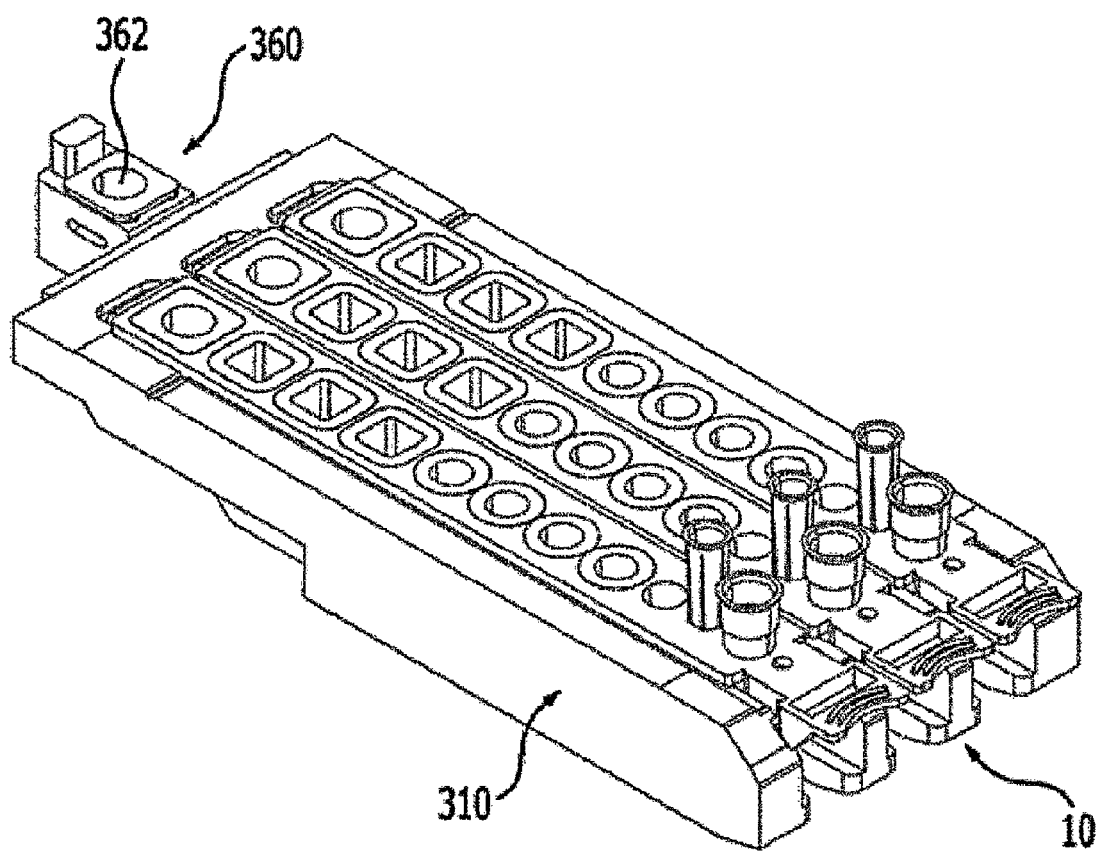
Figure 12:
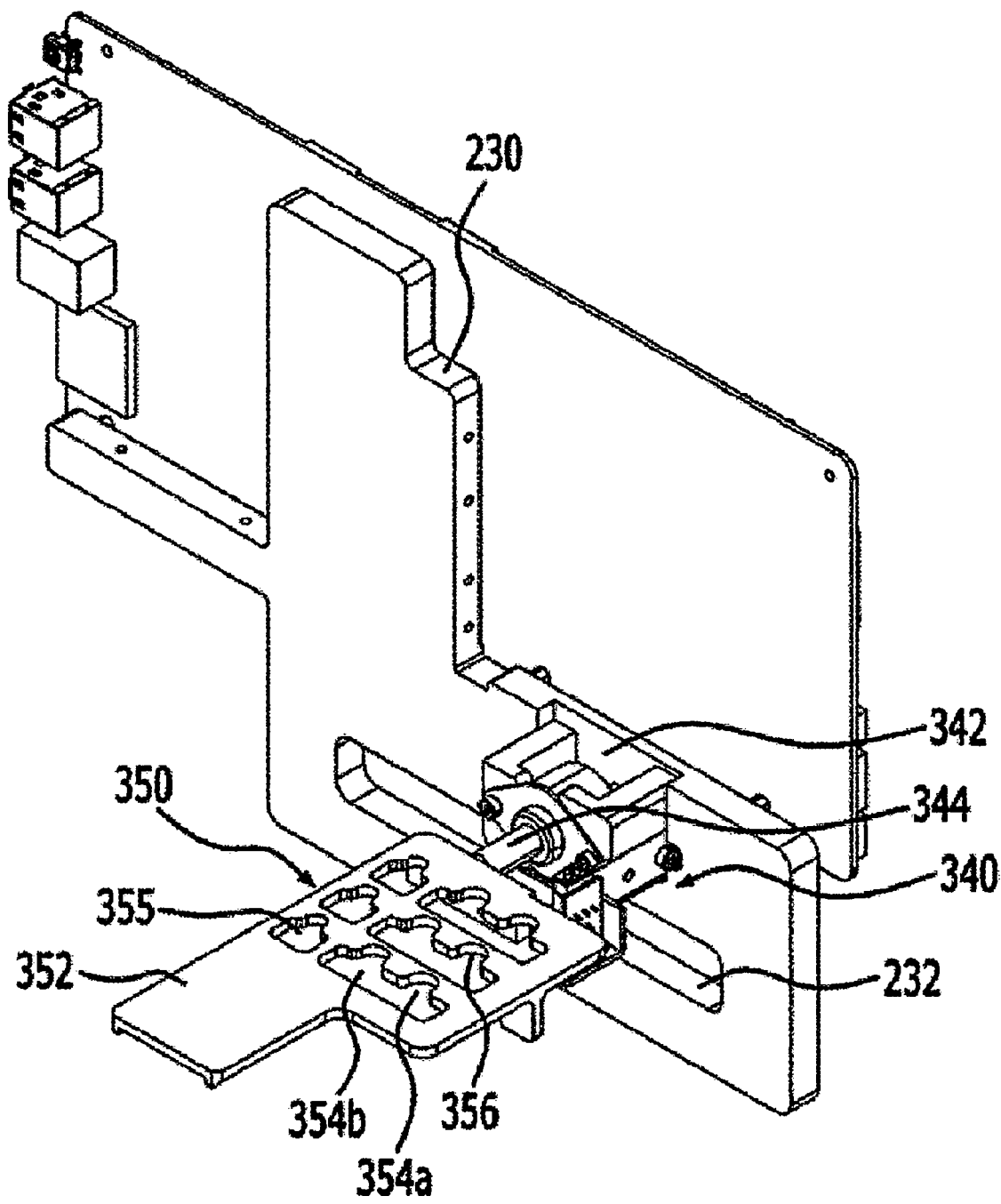
FIG. 12 is a view showing the structure of a remover module of the apparatus according to the embodiment of the present application.
Figure 13:
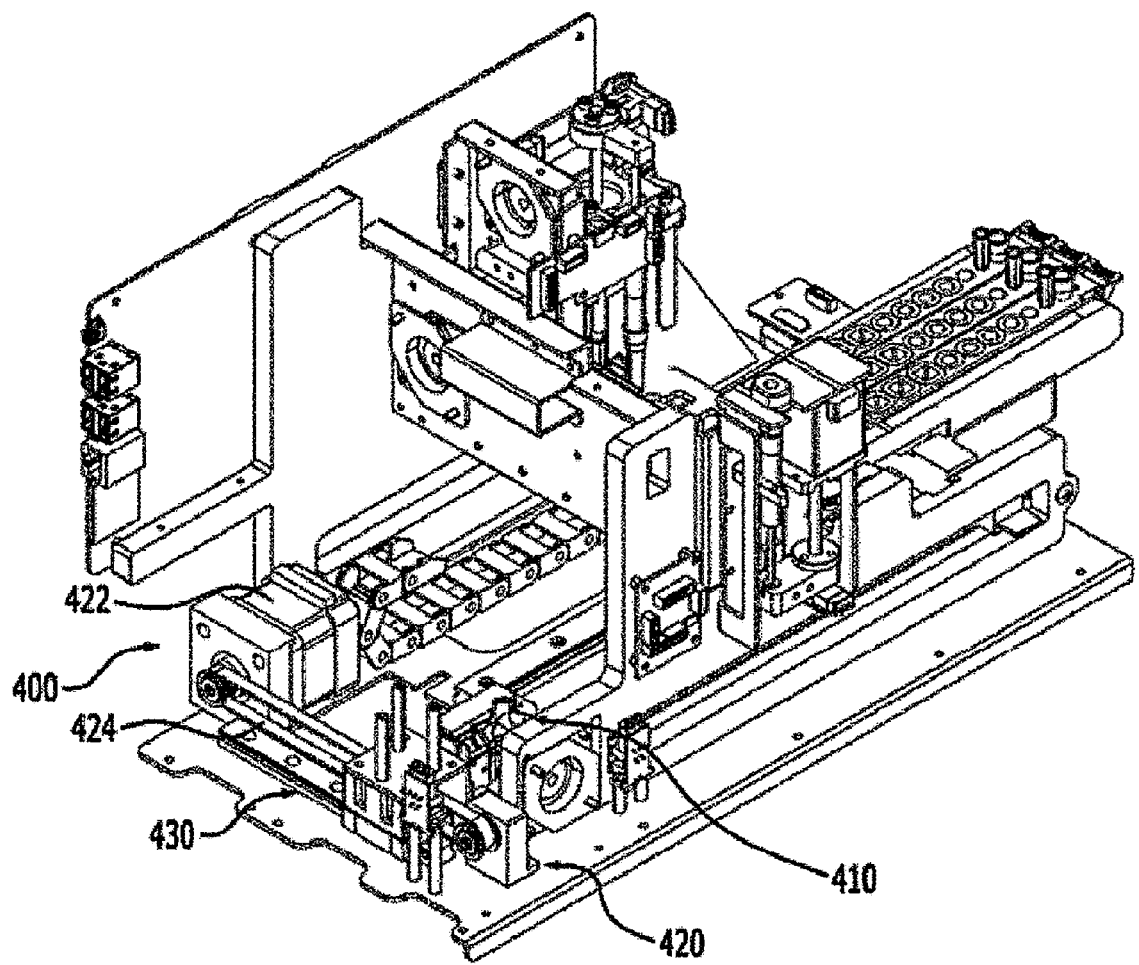
FIG. 13 is a view showing the rear side of the interior of the apparatus according to the embodiment of the present application.

FIGS. 10A, 10B, and 11 are views showing a holder 310 and a form in which the cuvette 10 is mounted in the holder 310 in the automated liquid-phase immunoassay apparatus according to the present invention. FIG. 12 is a view showing the structure of a remover module 340 of the automated liquid-phase immunoassay apparatus according to the present invention. FIG. 13 is a view showing the rear side of the interior of the automated liquid-phase immunoassay apparatus according to the present invention.

Hereinafter, the cuvette module 300 will be described.

The cuvette module 300 is provided in the housing 100 and is an apparatus for receiving the cuvette 10 and moving the received cuvette 10 in forward and backward directions.

The cuvette module 300 may include a holder 310, a holder-driving part 320, a holder guide part 330, and a remover module 340.

The holder 310 is a member in which the cuvette 10 may be seated. For example, the holder 310 may be positioned on the lower frame 210 and at the rear of the inlet-and-outlet port 120 in the housing 100. Thus, the cuvette 10 may be fitted into the holder 310 through the inlet-and-outlet port 120.

Meanwhile, the holder 310 may have a slot-shaped equipment channel 312 into which one or more cuvettes 10 are inserted so as to be equipped therein. The equipment channel 312 may have a constitution which is elongated in forward and backward directions and opened forwards.

An inspection hole 314 is formed at a rear end of the equipment channel 312. The inspection hole 314 is a portion formed through the equipment channel in upward and downward directions. Therefore, when the cuvette 10 is received and then equipped in the equipment channel 312 of the holder 310, the lower part of a portion of the rear part of the holder 310 is exposed through the inspection hole 314 in a downward direction. To be specific, the lower part of the detection chamber 16 positioned at the rear of the cuvette 10 may be exposed through the inspection hole 314 in a downward direction.

Further, a plurality of equipment channels 312 may be formed in the holder 310 so that the cuvettes 10 are inserted into the respective equipment channels 312 and inspection of a plurality of cuvettes 10 is performed. The plurality of equipment channels 312 may be positioned in a side-by-side arrangement in a single holder 310.

The lower part of the holder 310 is provided with a heat plate 316 and a heat plate power supply 318. This is to automatically control the temperatures of the cuvette and the reactants contained in the cuvette so as to maintain a constant temperature during the reaction, which ensures precision and accuracy of the inspection depending on the characteristics of the biological specimen, which is sensitive to temperature.

The heat plate 316 functions to heat the holder 310 so that the cuvette 10 and the specimen and the reactants contained in the cuvette are heated to a predetermined temperature and maintained at a specific temperature due to convection. The temperature is automatically controlled using the built-in program. A temperature sensor is employed for automatic control, and in the embodiment, the temperature sensor is used in the holder, the heat plate, and the apparatus. Since the temperature of the interior of the apparatus affects an optical system, the temperature sensor of the apparatus is used for temperature control of the interior of the apparatus. The temperature sensor of the heat plate controls the temperature of the heat plate, and the temperature sensor of the holder measures the temperature of the holder to thus control the heat plate in a feedback manner.

The holder-driving part 320 is a member which exerts forward and backward force on the holder 310. The holder-driving part 320 may include a movable body 322, to which the holder 310 is fixed, a driving motor, and a predetermined transmitting member for transmitting the power of the driving motor to the movable body 322.

The holder guide part 330 is provided so as to guide the displacement of the holder 310 in forward and backward directions. The holder guide part 330 may include a predetermined guide rail extending in forward and backward directions and a predetermined guide unit, which is connected to the guide rail so as to be movable forwards and backwards along the guide rail and which is also connected to the movable body 322.

The remover module 340 is a member for dispensing/mixing the reagents in different cuvettes for the immunoreaction time (incubation) after the use of the dispensing tip and the washing tip during an immunity inspection, or a member for removing the tip after the reaction is finished in each cuvette.

The remover module 340 may include a predetermined driving apparatus 342, which is fixed to the second side frame 230, and a predetermined remover plate 350, which is displaced using the driving apparatus 342. The driving apparatus 342 and the remover plate 350 may be connected through a predetermined shaft 344.

The remover plate 350 is located between the holder 310 and the dispenser module 500, as shown in FIG. 8. The remover plate 350 has a plate body 352, and the plate body 352 has a remover line in which three remover holes 354a, 354b, and 355 are formed in a line. The number of remover lines that are formed corresponds to the number of equipment channels 312 formed in the holder 310. The two remover holes 354a and 354b of the remover line are formed so that the holes are connected to each other and are located between the holder 310 and the dispenser module 500. Thus, a punching arm 552 and a straw arm 554, which will be described later, pass therethrough. A sampling arm 556 passes through one remover hole 355 formed alone in the remover line. Each of the remover holes 354a, 354b, and 355 may have a depression part 356 depressed to one side. Accordingly, in the state in which the dispensing tip 20 fastened to the sampling arm 556 and the washing tip 30 fastened to the straw arm 554 are located in corresponding remover holes 354a, 354b, and 355, the remover plate 350 is displaced to the left in a horizontal direction so that the sampling arm 556 is located at the depression part 356. A portion of the upper end of the dispensing tip 20 is located below the depression part of the plate. When the sampling arm or the straw arm is moved in an upward direction, force may be applied to a portion of the upper end of the dispensing tip 20 fastened to the sampling arm 556 or the washing tip 30 fastened to the straw arm 554, thus removing the tips from the respective arms.

The reaction occurring in the cuvette 10 used in the apparatus according to the present application requires a minimum of two or more incubation processes from start to detection. The provision of the remover module 340 in the apparatus according to the present application has a merit in that the reactions in the different cuvettes equipped in the different equipment channels 312 are prepared for an incubation time even when only one dispensing tip and one washing tip are used in one cuvette, as will be described later.

To be specific, in order to dispense/mix the reagents in the cuvette provided in the second equipment channel for a first incubation time, for which an immunoreaction occurs in the cuvette equipped in the first equipment channel 312, the dispensing tip 20 and the washing tip 30 which have been used in the first channel are temporarily stored at locations 21 and 32 corresponding to the first cuvette. After the lapse of the first incubation time, the dispensing tip 20 and the washing tip 30, which are temporarily stored, may be reused. That is, when the remover module 340 is not provided, the dispensing tip 20 or the washing tip 30, which has been used once in the first equipment channel, is not capable of being reused, but must be removed, and after the first incubation has elapsed, a new tip must be equipped, followed by a subsequent process. Accordingly, at least two dispensing tips 20 and at least two washing tips 30 are required per cuvette provided in the equipment channel. However, according to the present invention, since the remover module 340 is provided, there is a merit in that it is possible to perform the inspection process using only one dispensing tip 20 and one washing tip 30 for each cuvette.

The apparatus according to the present application may include a standard block 360. The standard block 360 may be fixed to the holder 310 so as to be integrally displaced together with the holder 310, and may be located at the rear of the holder 310. Preferably, the standard block 360 may be located at the rear of at least one inspection hole 314, among the above-described inspection holes 314.

The standard block 360 has a predetermined optical hole 362 formed in upward and downward directions therethrough, and the optical hole 362 may be provided with a predetermined optical means that is optically detected or captured.

In the embodiment, the standard block 360 includes the optical means.

In the embodiment, the optical means included in the standard block 360 includes a standard material for fluorescence measurement, having a predetermined fluorescence value, mounted thereon. The standard material for fluorescence measurement may be a material having appropriate excitation and emission wavelengths depending on the type of fluorescence detected in the material resulting from the reaction. In the embodiment, a 4-methylumbelliferone sodium salt having an excitation wavelength of 360 nm and an emission wavelength of 450 nm is used, without being limited thereto.

In another embodiment, the optical means included in the standard block 360 includes a standard material for absorbance measurement, having a visible color, mounted thereon. The standard material for absorbance measurement may be selected appropriately according to the absorbance region of the visible color detected in the material resulting from the reaction. In the embodiment, a glass plate, a plastic plate, a gel, and a suitable liquid solution are used, without limitation thereto.

In the optical assay, when the fluorescence or absorbance value of the material resulting from the reaction is measured after completion of the reaction, the standard fluorescence or absorbance provided using the standard block 360 is first scanned, and the signal value of the material resulting from the reaction is measured, which is represented by a ratio. This is to eliminate deviations between the instruments. The standard material is used to calculate the ratio to the measured value, and the ratio is compared to built-in data using a master calibration graph to thus accurately calculate the concentration of the analyte in the specimen.

When measuring the fluorescent or absorbance signal, the absolute values of the fluorescence values between the devices are generally different from each other. Accordingly, when the concentration is calculated using the absolute value of fluorescence, there is a problem in that an error may occur depending on the type of device. Therefore, when the ratio to the measured value is used with the standard material of the standard block, as in the present application, the error of the measured value between the devices is reduced, and accuracy and reproducibility are improved.

In yet another embodiment, the apparatus according to the present application may not include the standard block 360, or the standard block may not be used even if the apparatus includes the standard block 360. For example, when the signal detected in the material resulting from the reaction is chemiluminescent, the apparatus may not include the standard block, or the standard block may not be used, even if the apparatus includes the standard block. In this case, the apparatus may include a photodetector such as a PMT and an avalanche photodiode, and may be provided with a shutter embodied in hardware or software as a means for measuring the quantity of light for a predetermined constant time in order to measure the relative quantity of light. Accordingly, deviations in the detected signals between the apparatuses may be compared, followed by correction.

When the holder-driving part 320 is operated, the holder 310 may be displaced in forward and backward directions. When the holder 310 is moved in a backward direction by a predetermined distance, the standard block 360 fixed to the holder 310 is located on an optical reader 410, as will be described later. Accordingly, the fluorescent signal of the standard block 360 may be captured using the optical reader 410.

Further, when the holder 310 is moved to the rear end, the lower portion of the rear part of the holder 310 is located on an optical reading module 400, as will be described later. Therefore, when the holder 310 is moved to the rear end while the cuvette 10 is equipped in the equipment channel 312 of the holder 310, the lower portion of the detection chamber 16 positioned at the rear of the cuvette 10 may be exposed to the optical reading module 400 through the inspection hole 314.

Since the displacement of the holder 310 is guided by the holder guide part 330, the displacement may be stably performed without rocking. In particular, a pulley-belt-type holder-driving part 320 may be provided so as to prevent the occurrence of vibration and the inflow of foreign materials caused by friction generated during movement, thereby achieving more accurate inspection compared to a gear type.

Hereinafter, the optical reading module 400 will be described in detail.

The optical reading module 400 is provided for measuring the signal of the material resulting from the reaction in the cuvette 10. Preferably, the optical reading module 400 may include an optical reader 410, a reader-driving part 420, and a reader guide part 430.

The optical assay is performed by the optical reading module 400. The optical assay may include measurement of the fluorescent signal, the visible color, or the chemiluminescence of the material resulting from the reaction, and each of the signals may be defined with reference to the above.

The optical reader 410 is located below the holder 310 when the holder 310 is moved to the rear end. Therefore, when the holder 310 is moved backwards while the cuvette 10 is received in the holder 310, the detection chamber 16 of the cuvette 10 is located on the optical reader 410. Accordingly, the measurement of the fluorescence value for the material resulting from the reaction in the detection chamber 16 may be performed using the optical reader 410.

The optical reader 410 may read the signal of the material resulting from the reaction in the detection chamber 16 of the cuvette 10 to thus enable the qualitative and/or quantitative assay of a specific target analyte contained in the specimen.

Figure 16A:
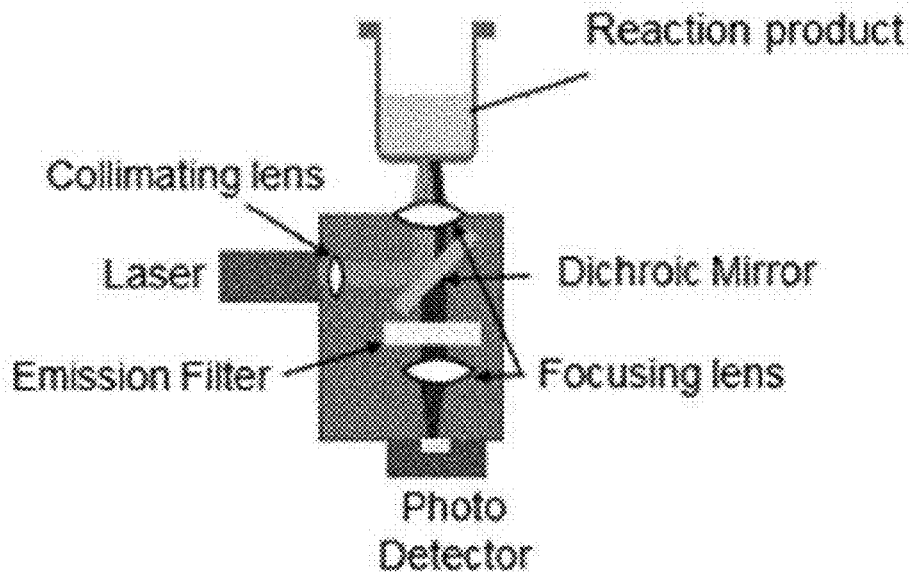
FIGS. 16A and 16B are views of a fluorescent optical system and a chemiluminescent optical system, respectively, that may be employed in the apparatus according to the embodiment of the present application.

In the embodiment, the optical reader 410 of the optical reading module detects a fluorescent signal. The optical reader 410 may radiate light having a specific wavelength depending on the type of the fluorescent material used in the detection of the analyte according to the present application, and may read the emitted light. For example, the optical reader may include the constitution shown in FIG. 16A. The optical reader 410 may be provided with a light source whose output is capable of being adjusted and which is capable of sufficiently exciting the fluorescent material for measurement of the fluorescent signal, that is, a predetermined light-emitting device. Examples of the light-emitting device include a Xenon lamp, a UV laser, or an LED (light-emitting diode). In the embodiment of the present application, an LED is used. The LED is less expensive than a Xenon lamp and a UV laser, and allows for smaller devices. In the present application, a feedback circuit is embedded in order to stabilize the temperature and the power supply when using the LED, and a diffusion-type LED is converted into a parallel light type using two pinholes. In particular, as described above, light may be radiated on the standard block 360 before measurement of the fluorescence value, so that gain is automatically adjusted using the quantity of fluorescence light that is captured, thereby adjusting the output of the light-emitting device to a constant value. This enables accurate concentration calculations.

Meanwhile, the optical reader 410 may have two or more light sources, and the light sources may generate light having different wavelengths. In addition, the fluorescences of different wavelengths may be measured separately. Therefore, the application range thereof to the diagnostic test method may be widened and the sensitivity thereof may be further improved. In addition, the optical reader 410 may have a barcode scanner function, so that when a predetermined barcode is provided in the cuvette 10, a predetermined signal and information exchanges may be performed through the corresponding barcode.

In yet another embodiment, the optical reader 410 of the optical reading module serves to measure the absorbance of the visible color of the material resulting from the reaction. The absorbance may be measured by radiating light on the material resulting from the reaction depending on the type of material used for detection of the analyte according to the present application. Meanwhile, the optical reader 410 includes a light source whose output is capable of being adjusted and which is capable of emitting an absorption wavelength region band suitable for absorbance measurement of the visible color. Examples of the light-emitting device may include a lamp, an LED, and a laser including an absorption wavelength band such as a white light source, but without limitation thereto.

Figure 16B:
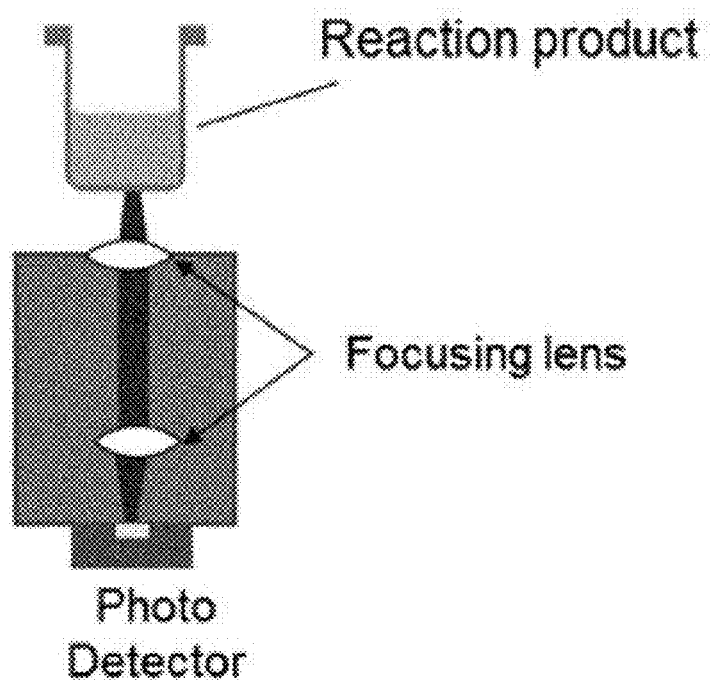

In still another embodiment, the optical reader 410 serves to measure a chemiluminescent signal of the material resulting from the reaction. The optical reader may detect light emitted depending on the type of chemiluminescent materials used for the detection of the analyte according to the present application, and includes a lens for trapping light and a photon detector so that the intensity of the light that is emitted is measured for each time. For example, the optical reader may include the constitution shown in FIG. 16B. The optical reader 410 does not include a light-emitting device or a light source, but instead includes a photodetector such as a PMT or an avalanche photodiode. Further, in order to measure the relative quantity of light, a shutter embodied in hardware or software may be provided as a means for measuring the quantity of light for a predetermined period of time. Accordingly, deviations in the detected signals between the apparatuses may be compared, followed by correction.

The reader-driving part 420 may be provided in the housing 100 and may move the optical reader 410 so that the optical reader 410 is located in any one cuvette 10 of a plurality of cuvettes 10, thereby inspecting the specimen in the corresponding cuvette 10.

For example, the reader-driving part 420 may include a predetermined driving motor 422 that enables the optical reader 410 to move leftwards and rightwards, a driven pulley 424, and a predetermined bracket for connecting the driven pulley 424 and the optical reader 410. Therefore, the optical reader 410 may be moved according to the operation of the driving motor.

The reader guide part 430 is provided to guide the displacement of the optical reader 410 in leftward and rightward directions. The reader guide part 430 may include a predetermined guide rail and a predetermined guide unit which is guided along the guide rail and fixed to the optical reader. Therefore, the movement of the optical reader in leftward and rightward directions may be unidirectionally guided with accuracy.

As described above, when the holder 310 is moved backwards by a predetermined distance, the standard block 360 at the lower portion of the rear part of the holder 310 is located on the optical reader 410 of the optical reading module 400. Accordingly, the optical reading module 400 first senses the fluorescent signal captured in the standard block 360 as a standard fluorescence. Subsequently, when the holder 310 is moved to the rear end while the cuvette 10 is equipped in the equipment channel 312 of the holder 310, the lower portion of the detection chamber 16 positioned at the rear of the cuvette 10 may be exposed to the optical reader 410 through the inspection hole 314, thereby performing optical measurement. As described above, the ratio of the fluorescent signal captured by the standard block 360 and the fluorescent signal captured in the detection chamber 16 is used for displaying. The optical reading module 400 may have a predetermined algorithm and a predetermined repetitive measurement algorithm that enable the calculation of the concentration of the analyte in the specimen by comparing the above ratio to built-in data using a master calibration graph.

As described above, since the measurement is performed in such a manner that the fluorescence value of the standard fluorescence mounted on the standard block 360 is compared to the fluorescence value of the specimen, measurement may be accurately performed. That is, according to a general conventional technology, there is a difference in fluorescence value between devices, and in order to reduce this difference, it is necessary to perform a calibration process for reducing the difference between instruments during most QC stages. Despite this process, however, it is difficult to completely eliminate the above-described difference due to changes in instruments or reagents. However, in the present invention, since the standard fluorescence mounted on the standard block 360 serves as a reference, the above problem may be solved.

Figure 14:
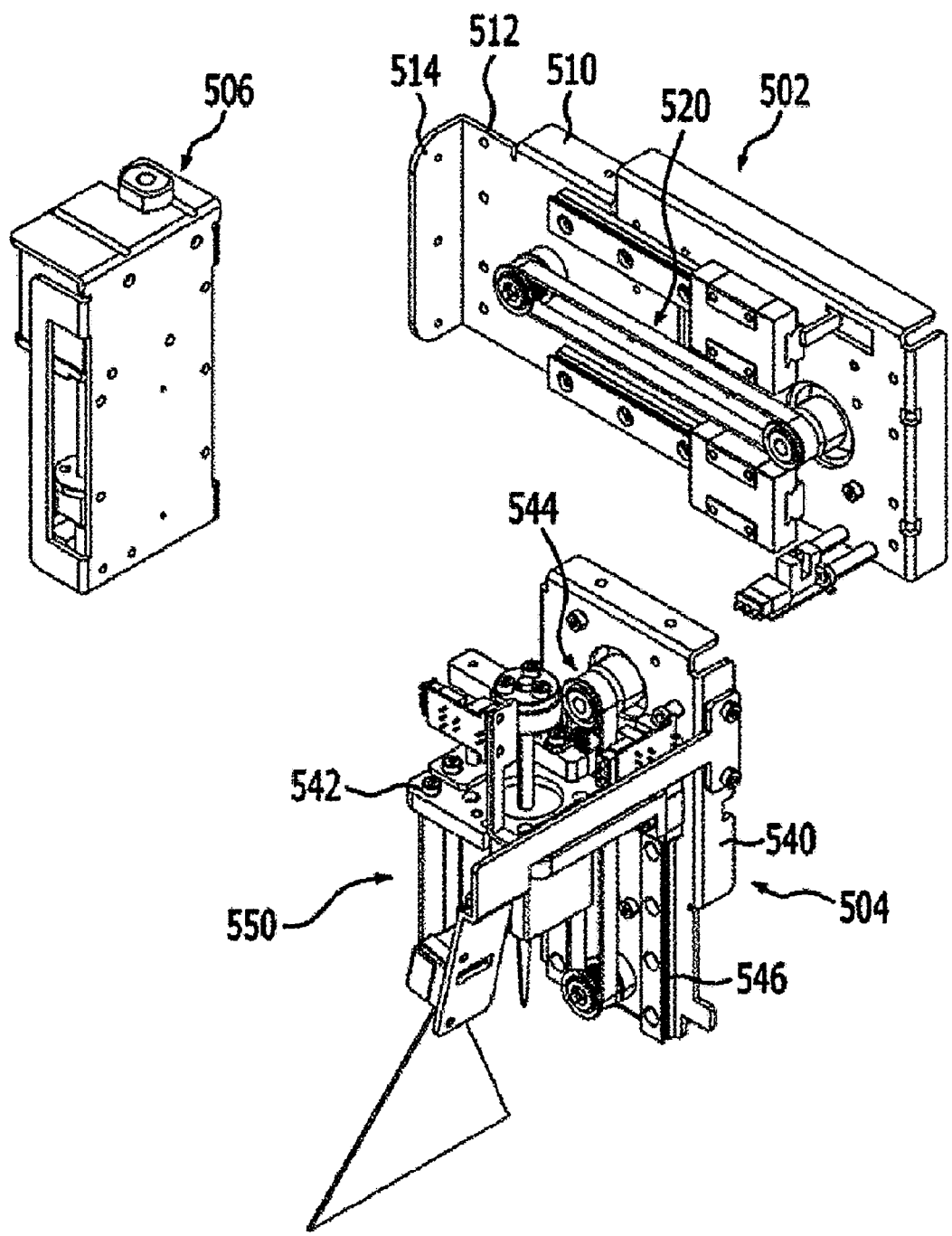
FIGS. 14 and 15 are views showing the structure of a dispenser module in an automated liquid-phase immunoassay apparatus according to the present invention.
Figure 15:
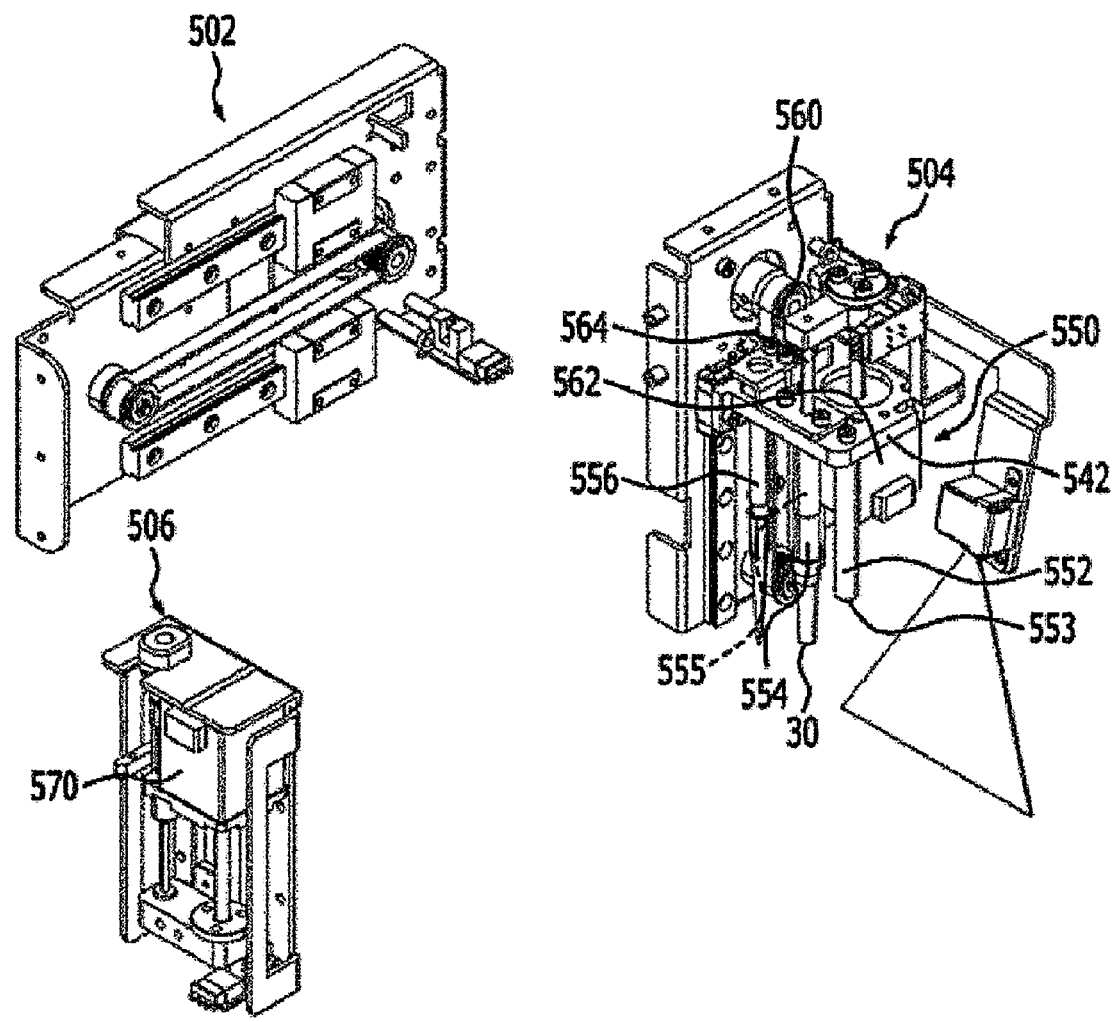

Hereinafter, the dispenser module 500 will be described. FIGS. 14 and 15 are exploded views showing the structure of the dispenser module 500 in the automated liquid-phase immunoassay apparatus 1 according to the present invention in different directions.

The dispenser module 500 is a module provided for distributing, dispensing, and washing specimens, reagents, and/or reactants.

The dispenser module 500 includes a driving unit 502, a dispenser unit 504, and a pump unit 506.

First, the driving unit 502 will be described.

The driving unit 502 serves to horizontally move the dispenser unit 504 leftwards and rightwards. Accordingly, the dispenser unit 504 may be horizontally moved by the driving unit 502 so that the dispenser unit 504 is located in a specific chamber on any one cuvette 10 of a plurality of cuvettes 10 located parallel to each other below the driving unit.

The driving unit 502 may include a fixing body 510 and a left-and-right horizontal driving part 520.

The fixing body 510 may have a predetermined area and may be elongated in leftward and rightward directions. The fixed body 510 may include a front body 512, extending in leftward and rightward directions, and a side body 514 which is provided on one side of the front body 512 and to which the pump unit 506 is fixed.

The left-and-right driving part 520 is a driving means that is positioned on the fixing body 510 and moves the dispenser unit 504, which will be described later, horizontally leftwards and rightwards. The left-and-right driving part 520 may include a predetermined driving motor for generating power and a predetermined moving bracket capable of being displaced leftwards and rightwards by the driving motor. Further, a predetermined guide means 530 for guiding the displacement of the moving bracket may be provided. In addition, a predetermined driven pulley member that transmits power may be included.

Next, the dispenser unit 504 will be described. The dispenser unit 504 may include a left-and-right moving body 540, an up-and-down moving body 542, an up-and-down driving part 544, and an arm unit 550.

The left-and-right moving body 540 is connected to the left-and-right driving part 520. As described above, the left-and-right driving part 520 may include the predetermined moving bracket, and the left-and-right moving body 540 may be connected to the moving bracket so as to be horizontally displaced leftwards and rightwards.

The up-and-down moving body 542 is positioned at the front of the left-and-right moving body 540. The up-and-down moving body may be displaced upwards and downwards by the up-and-down driving part 544.

The up-and-down driving part 544 is a driving means that is positioned on the left-and-right moving body 540 and moves the up-and-down moving body 542 in upward and downward directions. Further, the up-and-down driving part 544 may include a predetermined driving motor for generating power and a predetermined moving bracket capable of being displaced leftwards and rightwards by the driving motor. Further, a predetermined guide means 546 for guiding the displacement of the moving bracket in upward and downward directions may be provided. In addition, a predetermined driven pulley member that transmits power may be included.

The arm unit 550 is a member that is moved upwards and downwards by the up-and-down driving part 544 and is moved leftwards and rightwards by the driving unit 502. The arm unit 550 may include a punching arm 552, a sampling arm 556, and a straw arm 554, which are connected to the up-and-down moving body 542 and which extend in a downward direction at locations spaced apart from each other in a horizontal direction. Accordingly, the arm unit 550 may include an integrated module in which the punching arm 552, the sampling arm 556, and the straw arm 554 are integrally constituted.

The punching arm 552 is provided with a punching tip 553 at a bottom end thereof, and is a member for piercing and opening a sealing cover of the cuvette 10 to thus pierce a sealing portion covering the corresponding chamber of the cuvette 10.

The straw arm 554 is open in upward and downward directions to thus have upper and lower hollows 555. The straw arm 554 has an outer diameter suitable to be introduced into the introduction hole in the washing tip 30 so as to be fitted thereinto.

The sampling arm 556 is provided so that the dispensing tip 20 is fixed to the bottom end thereof. The sampling arm 556 may have an outer diameter suitable to be introduced into the dispensing tip 20 so as to be fitted thereinto.

Preferably, the punching arm 552, the straw arm 554, and the sampling arm 556 may be positioned in a line in forward and backward directions.

The washing unit 560 includes a servomotor and a magnetic beam 562.

The servomotor 562 may be fixed to the up-and-down moving body 542 and connected to the magnetic beam 562 to thus displace the magnetic beam 564 in upward and downward directions. Meanwhile, any predetermined driving apparatus capable of displacing the magnetic beam 564 upwards and downwards may be provided, without limitation to the servomotor 562.

The magnetic beam 564 is constituted in the form of a bar that extends in upward and downward directions, and is positioned in the upper and lower hollows 555 of the straw arm 554. The magnetic beam 554 may be magnetic and may be displaced in upward and downward directions by the servomotor 552 to thus enable mag-extraction for separating unreacted materials using magnetism.

The pump unit 506 is fixed to the side body 514 of the driving unit 502. The pump unit 506 is connected to the sampling arm 556 of the dispenser unit 504 through a predetermined pipe (not shown) so as to provide suction or discharge force when the dispensing tip 20 is inserted into the chamber of the cuvette 10 while being connected to the sampling arm 556. To be specific, the pump unit may provide the suction or discharge force to the dispensing tip 20 when the dispensing tip 20 is introduced into the chamber in the state in which the cuvette 10 is located at a specific site by the cuvette module 300 and the dispensing tip 20 is located on the chamber of the cuvette 10 by the driving unit 502. Preferably, the pump unit 506 may be provided with a motor 570 that enables rotary micro-step controlling so as to accurately adjust the amount of the specimen, the reagent, or the material resulting from the reaction upon suction or discharge thereof with respect to the dispensing tip 20.

Hereinafter, the operation of the automated liquid-phase immunoassay apparatus 1 according to the present invention will be described.

First, the cuvette 10 is received in the equipment channel 312 of the holder 310 of the apparatus 1. The dispensing tip 20 and the washing member 30 are equipped in the dispensing-tip-fitting hole 21 and the washing-member-fitting hole 31 formed in the cuvette. The dispensing tip 20 and the washing member 30 may be equipped either before or after the cuvette 10 is received in the equipment channel 312. Subsequently, the holder 310 is moved backwards according to the start command of the apparatus.

Subsequently, the dispenser module 500 is operated to thus open a sealing film (not shown) of the cuvette 10 by punching. In the punching process, a punching arm 552 is used. This punching process will be described. First, the punching arm 552 is located on the cuvette 10 by the driving unit. Subsequently, the punching arm 552 is moved upwards and downwards by the up-and-down driving unit 550, thus punching the sealing film of the cuvette 10. In this process, the cuvette module 300 may be operated to thus move the cuvette 10 forwards or backwards, thereby performing punching with respect to a plurality of chambers provided in the cuvette 10.

Subsequently, when punching is completed, the cuvette module 300 and the dispenser module 500 are operated so that the sampling arm 556 is located on the dispensing tip 20 fixed to the cuvette 10. Subsequently, the sampling arm 556 descends, so that the dispensing tip 20 is fitted into the sampling arm 556. After that, the dispensing tip 20 is used to distribute and dispense the specimen and/or the reagent. In this process, as in the punching process, the cuvette 10 is moved forwards or backwards by the cuvette module 300, and the dispensing tip 20 is moved upwards and downwards by the up-and-down driving part 544. During the above-described movement, the pump unit 506 is operated so as to perform distribution and dispensing using the dispensing tip 20. In addition, the operation by the pump unit 506 allows the specimen and/or the reagent to be mixed during the distribution and dispensing processes, so that the target reaction may occur in the reaction chamber 14 of the cuvette. The reaction process occurring in the cuvette 10 includes a plurality of steps and requires at least two incubation times per one cuvette. Thus, for a first incubation time, the dispensing tip 20 used in a first cuvette is removed by the remover plate 350 and is then located in the dispensing-tip-fitting hole 21 in the first cuvette in order to start a second cuvette reaction. After the completion of the first incubation time, the dispensing tip is reused for the next-stage reaction of the first cuvette.

When the distribution, dispensing, and reaction of the specimen and the reagent are completed as described above, the dispensing tip 20 is removed from the sampling arm 556 by the remover plate 350. Subsequently, the washing tip 30 is fitted into the straw arm 554. The washing tip 30 is introduced into the reaction chamber 14 and then the magnetic beam 564 is introduced into the washing tip 30, so that magnetic beads in the reaction chamber 14 are trapped by the surface of the washing tip 30. The reactive materials bonded to the magnetic beads are trapped therewith. After the washing tip 30 is moved into the washing chamber 15 in this state, when the magnetic beam 564 is lifted by the servomotor 562 to thus be separated from the washing tip 30, the magnetic beads trapped by the washing tip 30 are distributed in the washing chamber 15.

Meanwhile, in the above process, separation of the dispensing tip 20 and the washing tip 30 may be performed using the remover module 340. That is, after the dispensing tip 20 or the washing tip 30 is located in the remover hole 354 in the remover plate 350, when the remover plate 350 is moved so that the dispensing tip and the washing tip are moved onto the depression part 356 to thus move the sampling arm or the straw arm upwards, the top end of the tip equipped in the sampling arm and the straw arm is partially caught by the depression part 356, so that the dispensing tip 20 or the washing tip 30 may be separated from the sampling arm 556 or the straw arm 554.

To be specific, the separation of the dispensing tip and the washing tip 30 may be performed in the following sequence. The remover plate 350 is located between the holder 310 and the dispenser module 500. First, the remover hole 354 in the remover plate 350 is located over the washing-tip-fitting hole 21 and the dispensing-tip-fitting hole 31. Subsequently, after the dispensing tip 20 and the washing tip 30 are located in the washing-tip-fitting hole 21 and the dispensing-tip-fitting hole 31, the remover plate 350 comes into contact with the upper portion of the dispensing tip 20 or the washing tip 30. In this state, the dispenser module 500 is lifted, so that the dispensing tip 20 and the washing tip 30 are caught by the remover plate 350 to thus be separated from the sampling arm 556 and the straw arm 554. Then, the dispensing tip 20 and the washing tip 30 remain in the washing-tip-fitting hole 21 and the dispensing-tip-fitting hole 31, respectively. Therefore, since the dispensing tip 20 and the washing tip 30, which are separated from each other, remain in the washing-tip-fitting hole 21 and the dispensing-tip-fitting hole 31, respectively, the dispensing tip 20 and the washing tip 30 may be reused for the next-stage reaction in the same cuvette after the separation.

Subsequently, when the material resulting from the reaction is moved into the detection chamber 16, the optical reading module 400 is operated to perform optical inspection. The optical reader 410 is located below the detection chamber 16. Further, as described above, the detection chamber 16 may be light-transmissive, so that optical inspection of the reactants therein may be performed using the optical reader 410.

Prior to this, the optical reader 410 first reads the fluorescent signal of the standard block 360 located at the rear of the holder 310, and then reads the signal of the detection chamber 16. As described above, the deviation between the devices may be corrected using the signal captured in the standard block 360 as a standard fluorescence value.

Further, the apparatus according to the present application may further include a chip insertion part 130 which is provided in the housing and into which a chip containing assay information is inserted. The chip inserted into the chip insertion part is associated with the bar code of the cuvette. The barcode of the cuvette includes lot information on the target material to be assayed (item) and the cuvette, and is associated with the chip. The chip includes information on a master calibration curve necessary for calculating the concentration of the analyte and on driving of the apparatus depending on the type of the analyte in the specimen. Accordingly, the apparatus may be driven so as to be associated with the bar code, thus performing optimal inspection of various analytes depending on the type thereof. This makes it possible to easily inspect various analytes using one apparatus, and the reproducibility and reliability of the inspection may be improved. The barcode loads information via a barcode scanner that performs scanning thereof.

The inspection process according to the present invention will be sequentially described below.

Herein, a case where the cuvette 10 having the structure as shown in FIG. 6 is used will be described as an example. The cuvette 10 used in the inspection performed according to the present invention may have the structure shown in FIG. 6. To be specific, the cuvette may include a specimen-filling chamber 12, a buffer-solution-and-dilution chamber 13 that includes an MB buffer chamber 13a, a chamber 13b filled with a detection buffer such as ALP (alkaline phosphatase), a dilution-buffer chamber 13c, and a dilution chamber 13d, a reaction chamber 14, a washing chamber 15 that includes a first washing chamber 15a and a second washing chamber 15b, and a detection chamber 16.

First, after the bar code is recognized, the sealing of the cuvette 10 is punched using the punching arm 552 to thus perform opening. Subsequently, the dispensing tip 20 is fitted into the sampling arm 556 to thus be fixed. Subsequently, a predetermined volume of washing liquid is sampled from the first washing chamber 15a, and the washing liquid is dispensed into the MB buffer chamber 13a.

Subsequently, a predetermined dilution liquid is sampled from the dilution-buffer chamber 13c, and the sampled dilution liquid is dispensed to the sample chamber 12, thus performing a mixing process (three times). Subsequently, the diluted sample having a predetermined volume is sampled to thus be dispensed to the reaction chamber 14. Subsequently, after mixing in the chamber 13b filled with the detection buffer, a predetermined volume of the solution is sampled and then dispensed to the reaction chamber 14, followed by mixing (three times). Subsequently, a first incubation process is performed for a predetermined time at a specific temperature. Subsequently, after mixing in the MB buffer chamber 13a, a predetermined volume of the solution is sampled from the MB chamber 13a and then dispensed to the reaction chamber 14, followed by mixing. Subsequently, the dispensing tip 20 is removed using the remover module 340 and then located in the dispensing-tip-fitting hole 21 in the cuvette in which the reaction is performed. In addition, a second incubation process is performed for a predetermined time at a specific temperature.

Subsequently, the washing process is performed after a second incubation time elapses. First, the washing tip 30 is fitted into the straw arm 554, and the magnetic beam 564 is introduced into the straw arm 554 to thus remain in the reaction chamber 14 for a predetermined time, introduced into the first washing chamber 15a, and moved upwards and downwards several times, thereby performing the washing process. Subsequently, the magnetic beam 564 is introduced again into the straw arm 554, is introduced into the second washing chamber 15b, and is moved upwards and downwards several times, thereby performing the washing. Subsequently, the magnetic beam 564 is introduced again into the straw arm 554 and is introduced into the detection chamber 16, and the washing tip 30 is then removed.

Subsequently, after a third incubation process for a predetermined time, an optical measurement process is performed. The results (concentration) derived from the optical measurements may be outputted using a display and a printer. In addition, the reaction in another cuvette may be performed while the incubation proceeds. For example, when the apparatus according to the present application includes three cuvettes, the step in the first cuvette is started to thus perform first incubation, during which the first incubation in the second cuvette is started, followed by starting of the first incubation in the third cuvette. Subsequently, the first incubation in the first cuvette is terminated, and a subsequent process is started to thus perform second incubation. During the second incubation time in the first cuvette, the respective corresponding second incubations are sequentially started in the second and third cuvettes. Subsequently, after the second incubation in the first cuvette is terminated, third incubation is performed, and the respective corresponding third incubations are sequentially started in the second and third cuvettes. Progression in this way may save up to about 50% of the time compared to performing the respective reactions independently in three cuvettes. For example, when three reactions that each require 20 minutes are separately performed, about 60 minutes is required, but a total of 30 minutes is required when the apparatus according to the present application is used.

After proceeding in the same manner as described above until all the processes up to the washing process in the first, second, and third cuvettes are completed, the fluorescent signals with respect to the first, second, and third cuvettes are sequentially detected in the detection chambers.

In this respect, the present application is directed to a method of detecting an analyte in a biological specimen using the apparatus according to the present application, the method including the processes as described above.

In the automated liquid-phase fluorescence immunoassay apparatus 1 according to the present invention, it is possible to perform dispensing and reaction of the specimen, separation (purification) of the material resulting from the reaction by a washing module using magnetic beads, and detection/reading of the material resulting from the reaction using a liquid-phase specimen optical system with high sensitivity and high specificity, compared to the conventional methods. In particular, according to the present invention, it is possible to accurately and quickly perform the inspection for detection and reading/assay of the material resulting from the reaction after the dispensing of the specimen and the reaction between the reagent and the specimen using one integrated system. It is also possible to shorten an inspection time, improve the accuracy and reproducibility of the inspection, and reduce the steps included in the entire inspection and the input costs.

Further, the arm unit 550 provided in the automated liquid-phase fluorescence immunoassay apparatus 1 according to the present application includes an integrated module that is integrally provided with the punching arm 552, the sampling arm 556, and the straw arm 554, which enables the control of locations in upward and downward directions using one driving motor upon dispensing of a pump (pump dispenser), driving of a puncher, and separation of the washing-and-dispensing tip 20 and the washing tip 30. Therefore, it is possible to reduce the size and manufacturing costs, unlike the case where each module is constituted by a respective driving motor. In addition, because the arm unit 550 includes an integrated module, the arm unit is designed so that each arm is operated while being connected to one up-and-down driving part 550 and there is no interference between the drives. By using the arm unit 550 including the integrated module as described above, it is possible to greatly reduce the size and manufacturing cost of the entire device.

Further, the pump unit 506 included in the apparatus according to the present application employs a motor capable of performing rotary micro-step control, so that the amount of the specimen, the reagent, or the material resulting from the reaction may be accurately adjusted using the dispensing tip upon suction or discharge for separation and dispensing thereof.

In addition, the apparatus according to the present application is provided with the remover module 350. Accordingly, the dispensing tip 20 and the washing tip 30 that are used may be easily separated from the dispenser module 500. In addition, the separation is performed using the remover module 340, so that the dispensing tip 20 and the washing tip 30 may be reused after separation.

Further, the apparatus according to the present application may include the standard block 360, thus performing the inspection with respect to a ratio to a standard fluorescence using the standard fluorescence.

In summary, the apparatus according to the present application is a convenient automated immune inspection apparatus which does not require a separate reagent preparation process because a reagent is integrally prepared, and is capable of simultaneously performing a plurality of different inspections, for example, three different inspections. In the conventional case, the same inspections are simultaneously performed. Further, an integrated module that is capable of performing all of punching, distribution and dispensing of reagents and washing is employed, and a system that is capable of minimizing the deviation of optical systems and instruments using standard fluorescence is employed. Further, the reaction temperature of the reagent is capable of being controlled so as to remain constant. Further, the dispensing tip and the washing tip, which are consumables, are capable of being reseated on the cuvette, which eliminates the need for a separate compartment (trash) to discard the tip. In the case of instruments that use consumable dispensing tips and washing tips, the dispensing tip is discarded after use. This is because the dispensing tip should not be used for other reagent inspections due to contamination. Further, the apparatus 1 of the present application needs to replace the dispensing tip to prepare for the reaction of the other reagent during the reaction of the reagent in the cuvette. The used tip is seated in the cuvette 1, and a preparation process is performed using the dispensing tips of the cuvettes 2 and 3. Thereafter, the dispensing tip of the cuvette 1 is re-equipped to thus prepare for a second incubation process. If the dispensing tip used in the first incubation is discarded, a new tip must be employed in the second incubation preparation. After the present instrument is seated on a cartridge, the dispensing and mixing of the other cartridges are performed, and the tip of the original cartridge is then reused to thus perform the next process. Accordingly, the number of each of consumable dispensing tips and washing tips that are consumed may be limited to one. Further, there is no need to prepare the dispensing tip in the instrument, which is advantageous in terms of space and enables more compact instruments to be designed.

Although a preferred embodiment of the present invention has been described for illustrative purposes, it is to be understood that the scope of the present invention is not limited thereto, and various modifications and reformations by those skilled in the art using the basic concept of the present invention as defined in the accompanying claims fall within the scope of the present invention.

DESCRIPTION OF THE STANDARD NUMERALS

10: cuvette
12: specimen-filling chamber
13: buffer-solution-and-dilution chamber
14: reaction chamber
15: washing chamber
16: detection chamber
20: dispensing tip
21: dispensing-tip-fitting hole
30: washing tip
31: washing-tip-fitting hole
100: housing
110: display part
120: inlet-and-outlet port
130: chip insertion part
200: frame
210: lower frame
220: first side frame 230: second side frame
240: rear frame
300: cuvette module
310: holder
312: equipment channel
314: inspection hole
316: holder heat plate
318: heat plate power supply
320: holder-driving part
330: holder guide part
340: remover module
342: driving apparatus
350: remover plate
352: plate body
354, 355: remover holes
356: depression part
360: standard block
362: optical hole
400: optical reading module
410: optical reader
420: reader-driving part
430: reader guide part
500: dispenser module
502: driving unit
504: dispenser unit
506: pump unit
510: fixing body
512: front body
514: side body
520: left-and-right driving part
530: guide means
540: left-and-right moving body
542: up-and-down moving body
544: up-and-down driving part
550: arm unit
552: punching arm
553: punching tip
554: straw arm
555: upper and lower hollows
556: sampling arm
560: washing unit
562: servomotor
564: magnetic beam
570: motor

What is claimed is:

1. A liquid-based immune reaction analysis device using a cuvette having a plurality of chambers, wherein the plurality of chambers includes chambers filled with a sample, a reagent and magnetic beads, and the plurality of chambers includes chambers seated with a dispensing tip of a tubular shape and a washing tip of a cup shape, the liquid-based immune reaction analysis device comprising:
   a cuvette module to which the cuvette is mounted;
   a sampling arm in which the dispensing tip seated on the cuvette is detachably fitted to one end of the sampling arm;
   a straw arm in which a hollow is formed inside, the washing tip seated on the cuvette being detachably fitted to one end of the straw arm, and a magnetic body in the form of a beam configured to move up and down through the hollow; and
   a remover module having a remover plate,
   wherein the remover module detaches the dispensing tip from the sampling arm and the washing tip from the straw arm by using the remover plate, and places the dispensing tip and the washing tip on the cuvette,
   wherein the magnetic body is configured to attach the magnetic beads to the washing tip when moved down in the hollow of the straw arm.

2. The analysis device of claim 1, wherein the analysis device further comprises an optical reading module for detecting a reaction product of the reagent and the sample in the cuvette, wherein the optical reading module includes an optical reader that reads a fluorescent signal, a visible color, or a chemiluminescent signal generated from the reaction product in the cuvette.

3. The analysis device of claim 1, wherein the cuvette module includes a heat plate for maintaining a temperature of the mounted cuvette.

4. The analysis device of claim 1, wherein the remover plate includes a plurality of holes penetrating vertically and having a depression on one side of the remover.

5. The analysis device of claim 2, wherein the cuvette module includes a block in which a standard material is accommodated, and the optical reading module detects a signal for correcting a deviation from the standard material.

6. The analysis device of claim 1, wherein the cuvette module includes a plurality of channels on which the cuvette is mounted, and the dispensing tip and the washing tip detached by the remover module are placed back on the cuvette.

* * * * *